United States Patent
Kang et al.

(10) Patent No.: US 9,801,898 B2
(45) Date of Patent: Oct. 31, 2017

(54) GLUTAMATE DEHYDROGENASE 1 INHIBITORS AND METHODS OF TREATING CANCER

(71) Applicant: Emory University, Atlanta, GA (US)

(72) Inventors: Sumin Kang, Decatur, GA (US); Jing Chen, Atlanta, GA (US); Lingtao Jin, Atlanta, GA (US)

(73) Assignee: Emory University, Atlanta ( * ) Notice: Subject to any disclaimer, the term of this patent is extended or adjusted under 35 U.S.C. 154(b) by 0 days.

(21) Appl. No.: 15/017,095

(22) Filed: Feb. 5, 2016

(65) Prior Publication Data
US 2016/0228466 A1 Aug. 11, 2016

Related U.S. Application Data

(60) Provisional application No. 62/112,937, filed on Feb. 6, 2015.

(51) Int. Cl.
*A61K 31/713* (2006.01)
*A61K 31/122* (2006.01)
*A61K 45/06* (2006.01)

(52) U.S. Cl.
CPC .......... *A61K 31/713* (2013.01); *A61K 31/122* (2013.01); *A61K 45/06* (2013.01)

(58) Field of Classification Search
None
See application file for complete search history.

(56) References Cited

U.S. PATENT DOCUMENTS

| 6,686,393 B1 | 2/2004 | Hughes |
| 9,040,567 B2 | 5/2015 | Deng |
| 9,402,850 B2 | 8/2016 | Deng |

(Continued)

FOREIGN PATENT DOCUMENTS

WO WO 2012166617 * 12/2012

OTHER PUBLICATIONS

The Organic Chemistry of Drug Design and Drug Action, Silverman, Academic Press, 1992, pp. 352-355, see pp. 354-355.*

(Continued)

*Primary Examiner* — Karl J Puttlitz
(74) *Attorney, Agent, or Firm* — Emory Patent Group

(57) ABSTRACT

This disclosure relates to methods of treating or preventing cancer comprising administering an effective amount of a glutamate dehydrogenase 1 inhibitor to a subject in need thereof. In certain embodiments, the inhibitor has Formula I:

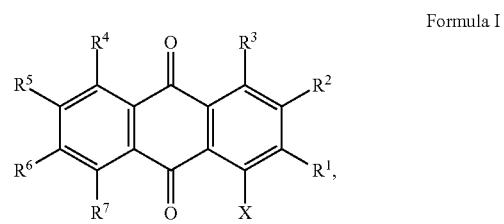

Formula I prodrugs, derivatives, or salts thereof wherein the substituents are reported herein. In certain embodiments, the inhibitor is purpurin, derivative, or salt thereof. In certain embodiments, the inhibitor is 2-allyl-1-hydroxyanthracene-9,10-dione, prodrugs, derivatives, or salts thereof.

4 Claims, 23 Drawing Sheets

(56) References Cited

U.S. PATENT DOCUMENTS

| | | |
|---|---|---|
| 2007/0238784 A1 | 10/2007 | Chien |
| 2008/0089945 A1 | 4/2008 | Xu |
| 2009/0226431 A1 | 9/2009 | Habib |
| 2010/0249224 A1 | 9/2010 | Smith |
| 2011/0224414 A1 | 9/2011 | Wang |
| 2014/0294818 A1 | 10/2014 | Chen |

OTHER PUBLICATIONS

Cichewicz et al., Life Sciences 74 (2004) 1791-1799.*
Jin et al. Glutamate Dehydrogenase 1 Signals through Antioxidant Glutathione Peroxidase 1 to Regulate Redox Homeostasis and Tumor Growth, Cancer Cell 27, 257-270, 2015.
Li et al. Green tea polyphenols modulate insulin secretion by inhibiting glutamate dehydrogenase, J Biol Chem. 2006, 281(15)10214-21.
Li et al. Novel inhibitors complexed with glutamate dehydrogenase: allosteric regulation by control of protein dynamics, J Biol Chem. 2009, 284(34):22988-3000.
Sangthong et al. Anthracene-9, 10-dione derivatives induced apoptosis in human cervical cancer cell line (CaSki) by interfering with HPV E6 expression, European Journal of Medicinal Chemistry 77 (2014) 334e342.
Vander Heiden, Targeting cancer metabolism: a therapeutic window opens, Nature Reviews Drug Discovery 10, 671-684 (2011).
Whitelaw et al. Inhibitors of glutamate dehydrogenase block sodium-dependent glutamate uptake in rat brain membranes, Front Endocrinol (Lausanne). 2013, 4:123.

* cited by examiner

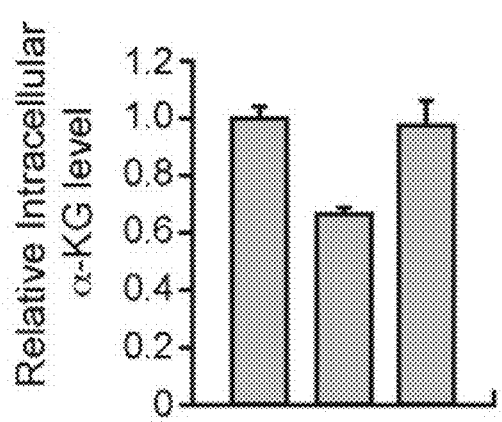 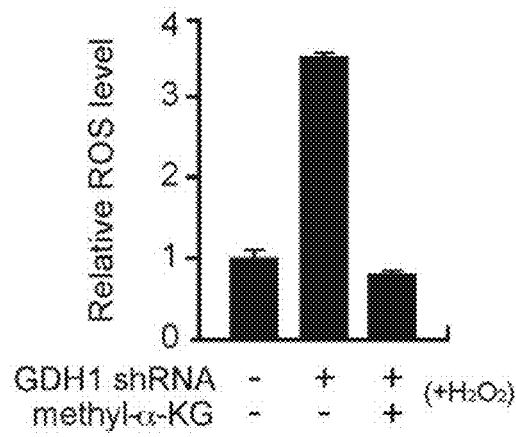
FIG. 3I
FIG. 3J
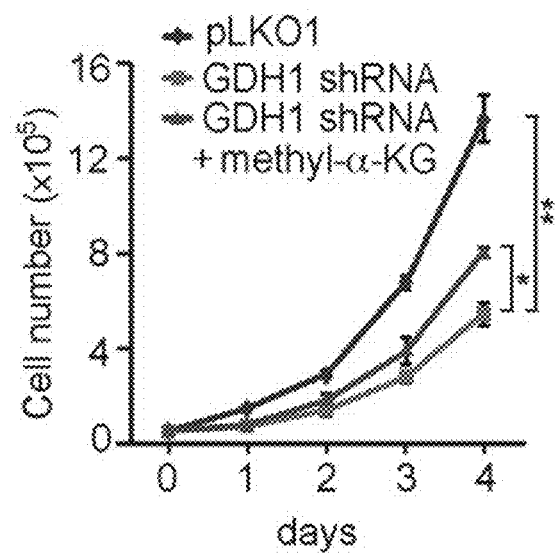
FIG. 3K

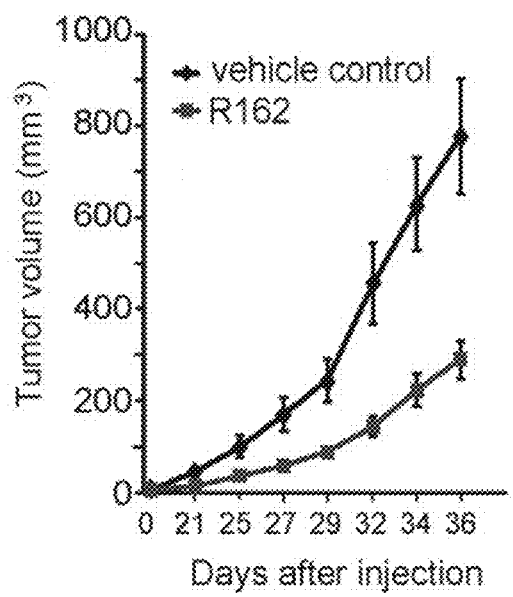
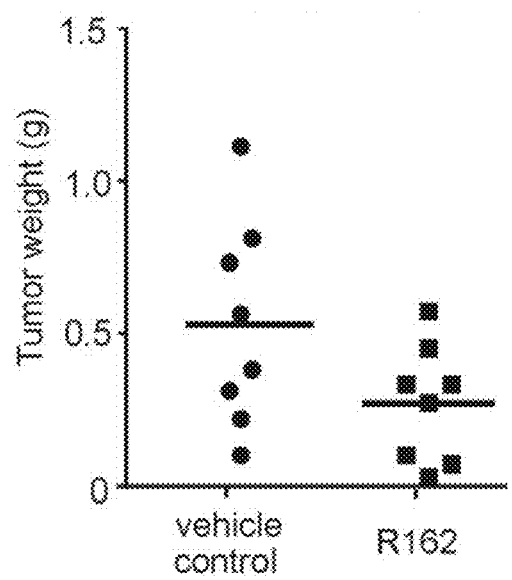
FIG. 7A
FIG. 7B
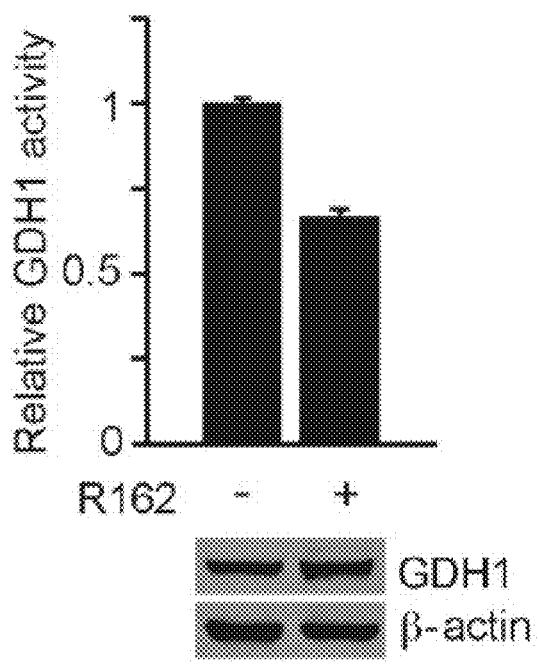
FIG. 7C

GLUTAMATE DEHYDROGENASE 1 INHIBITORS AND METHODS OF TREATING CANCER

CROSS REFERENCE TO RELATED APPLICATIONS

This application claims priority to U.S. Provisional Application 62/112,937 filed Feb. 6, 2015, hereby incorporated by reference in its entirety.

BACKGROUND

Cancer causes a substantial portion of all human deaths. Many cancers, such as lung cancer, continue to be resistant to known chemotherapy regiments; thus, there is a need to identify improved treatment methods.

Emerging evidence indicates that impaired cellular metabolism is the defining characteristic of nearly all cancers regardless of cellular or tissue origin. One predominant metabolic abnormality is that cancer cells take up glucose at higher rates than normal tissue and favor aerobic glycolysis. In addition to the dependency on glycolysis, cancer cells have another atypical metabolic characteristic, that of increased rates of glutamine metabolism. Although the requirement for mitochondrial ATP production is reduced in glycolytic tumor cells, the demand for tricarboxylic acid cycle (TCA) cycle-derived biosynthetic precursors and nicotinamide adenine dinucleotide phosphate, reduced form (NADPH) is unchanged or even increased. In order to compensate for these changes and to maintain a functional TCA cycle, cancer cells often rely on elevated glutaminolysis.

Glutaminolysis is a mitochondrial pathway that involves the initial deamination of glutamine by glutaminase (GLS), yielding glutamate and ammonia. Glutamate is then converted to alpha-ketoglutarate (alpha-KG), a TCA cycle intermediate, to produce both ATP and anabolic carbons for the synthesis of amino acids, nucleotides, and lipids. The conversion of glutamate to alpha-KG is catalyzed by either glutamate dehydrogenase 1 (GDH1, also known as GLUD1, GLUD, GDH) or other transaminases, including glutamate pyruvate transaminase 2 (GPT2, also known as alanine aminotransferase), and glutamate oxaloacetate transaminase 2 (GOT2, also known as aspartate aminotransferase), which convert a-keto acids into their corresponding amino acids in mitochondria. Fluxes of these enzymes are commonly elevated in human cancers. Glutaminolysis also supports the production of molecules, such as glutathione and NADPH, which protect cells from oxidative stress. Mounting evidence suggests that many types of cancer cells have tumor-specific redox control alterations, with increased levels of reactive oxygen species (ROS) compared with normal cells. A moderate increase in ROS can promote cell proliferation and differentiation, whereas excessive amounts of ROS can cause oxidative damage to proteins, lipid, and DNA. Therefore, maintaining ROS homeostasis is crucial for cell growth and survival. Cells control ROS levels by balancing ROS generation with their elimination by ROS-scavenging systems such as glutathione peroxidase (GPx), gluthathione reductase (GSR), thioredoxin (Trx), superoxide dismutases (SODs), catalase (CAT), and peroxiredoxin (PRX).

Alpha-KG, a product of GDH1 and a key intermediate in glutamine metabolism, is known to stabilize redox homeostasis in cells. Although elevated glutaminolysis and altered redox status in cancer cells has been theoretically justified, the mechanism by which alpha-KG regulates redox and whether this regulation is crucial for tumorigenesis and tumor growth remain elusive.

Jin et al. report Glutamate Dehydrogenase 1 signals through antioxidant Glutathione Peroxidase 1 to regulate redox homeostasis and tumor growth. Cancer Cell 27, 257-270.

References cited herein are not an admission of prior art.

SUMMARY

This disclosure relates to methods of treating or preventing cancer comprising administering an effective amount of a glutamate dehydrogenase 1 inhibitor to a subject in need thereof. In certain embodiments, the inhibitor has Formula I:

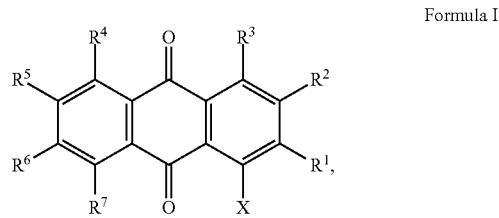

Formula I prodrugs, derivatives, or salts thereof wherein the substituents are reported herein. In certain embodiments, the inhibitor is purpurin, derivative, or salt thereof. In certain embodiments, the inhibitor is 2-allyl-1-hydroxyanthracene-9,10-dione, prodrugs, derivatives, or salts thereof.

In certain embodiments, the inhibitor is epigallocatechin gallate, prodrugs, derivatives, or salts thereof.

In certain embodiments, the inhibitor is iRNA that targets GLUD1 mRNA. In certain embodiments, the inhibitor is shRNA designed to knock down gene expression.

BRIEF DESCRIPTION OF THE FIGURES

FIG. 3I shows data when H1299 cells were treated in the presence and absence of 0.5 mM methyl-alpha-KG for Intracellular alpha-KG level.

FIG. 3J shows data for ROS production.

FIG. 3K shows data for proliferation rates.

FIG. 7A shows data on R162 administration and tumor growth in H1299 xenograft mice model.

FIG. 7B shows tumor weight examined at the experimental endpoint.

FIG. 7C shows data on GDH1 protein and activity levels in dissected tumor samples. GDH1 expression in tumor lysates is shown by western blotting.

DETAILED DISCUSSION

Figure 1A:
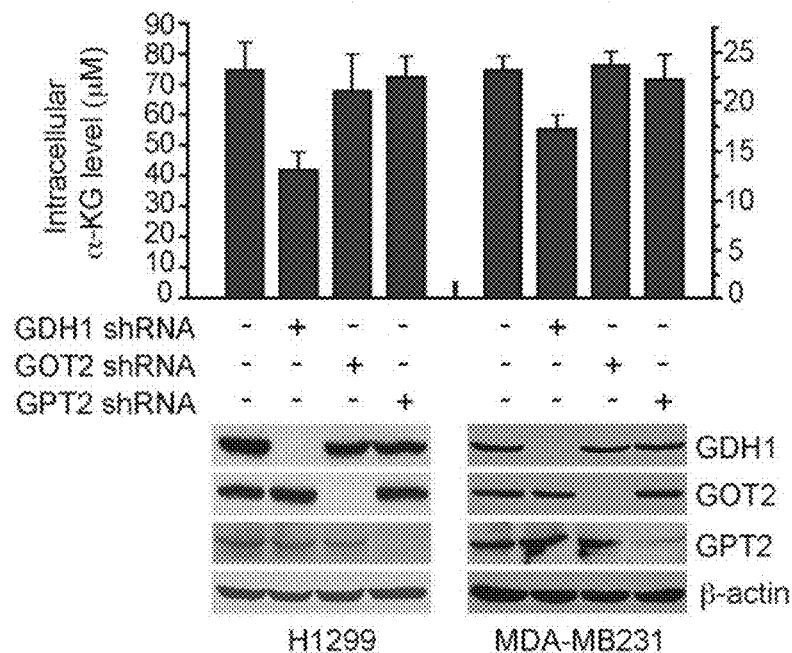
FIG. 1A shows data indicating GDH1 predominantly regulates alpha-KG production in cancer cells and is upregulated in human lung and breast cancers. Intracellular alpha-KG levels were determined in human lung cancer H1299 and breast cancer MDA-MB231 cells with stable knockdown of GDH1, GOT2, or GPT2. Expression of GDH1, GOT2, and GPT2 in H1299, and MDA-MB231 cells are shown by western blot analyses. Beta-actin was used as a loading control.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of immunology, medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

In this specification and in the claims that follow, reference will be made to a number of terms that shall be defined to have the following meanings unless a contrary intention is apparent.

As used herein, the term "combination with" when used to describe administration with an additional treatment means that the agent may be administered prior to, together with, or after the additional treatment, or a combination thereof, however provides a therapeutic amount of both agents, e.g., both at sufficient concentrations in the blood at the same time.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample particle compared to a control without the particle. It can also be identified by a change in relevant biomarker or gene expression profile, such as PSA for prostate cancer, HER2 for breast cancer, or others.

As used herein, "alkyl" means a noncyclic straight chain or branched, unsaturated or saturated hydrocarbon such as those containing from 1 to 10 carbon atoms. A "higher alkyl" refers to unsaturated or saturated hydrocarbon having 6 or more carbon atoms. A "C8-C18" refers to an alkyl containing 8 to 18 carbon atoms. Likewise a "C6-C22" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulphur which may be saturated or unsaturated (but not aromatic), monocyclic or polycyclic, and wherein the nitrogen and sulphur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkoxyalkyl" refers an alkyl group as defined above with the indicated number of carbon atoms attached through an alkyl bridge (i.e., —CH$_2$—O—CH$_2$CH$_3$).

"Alkylamino" refers an alkyl group as defined above with the indicated number of carbon atoms attached through an amino bridge. An example of an alkylamino is methylamino, (i.e., —NH—CH$_3$).

"Alkylthio" refers to an alkyl group as defined above with the indicated number of carbon atoms attached through a sulfur bridge. An example of an alkylthio is methylthio, (i.e., —S—CH$_3$).

"Alkanoyl" refers to an alkyl as defined above with the indicated number of carbon atoms attached through a carbonyl bride (i.e., —(C=O)alkyl).

The terms "cycloalkyl" and "cycloalkenyl" refer to mono-, bi-, or tri homocyclic ring groups of 3 to 15 carbon atoms which are, respectively, fully saturated and partially unsaturated.

The terms "halogen" or "Hal" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, adding a hydroxyl group, replacing an oxygen atom with a sulfur atom, or replacing an amino group with a hydroxyl group, oxidizing a hydroxyl group to a carbonyl group, reducing a carbonyl group to a hydroxyl group, and reducing a carbon-to-carbon double bond to an alkyl group or oxidizing a carbon-to-carbon single bond to a double bond. A derivative optional has one or more, the same or different, substitutions. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Glutamate Dehydrogenase 1 Signals through Antioxidant Glutathione Peroxidase 1 to Regulate Redox Homeostasis and Tumor Growth Although it is not intended that embodiments of this disclosure be limited by any particular mechanism, it is believed that cancer is associated with a mechanism by which the mitochondrial GDH1 contributes to redox homeostasis. GDH1 controls the intracellular levels of its product alpha-KG and the subsequent metabolic intermediate fumarate, which binds and activates the ROS scavenging enzyme GPx1, providing metabolic advantages to cancer cell proliferation and tumor growth. Although three enzymes, including GDH1, GOT2, and GPT2, are reported to convert glutamate to alpha-KG, experiments herein indicate that GDH1 plays a predominant role in maintaining the physiological levels of alpha-KG in cancer cells. GDH1 may also play a critical role in alpha-KG-dependent biological functions, including not only the TCA cycle but also epigenetic regulations involving diverse alpha-KG-dependent enzymes such as histone and DNA dioxygenases that regulate genome-wide histone and DNA methylation.

Emerging evidence has demonstrated the importance of glutamine as an alternative carbon source for both bioenergetics and anabolic biosynthesis in addition to glucose. Consistently, experiments disclosed herein indicate that suppression of GDH1 resulted in decreased glutaminolysis, which renders cancer cells more dependent on glycolysis and more sensitive to stress conditions such as glucose deprivation, but not low oxygen. Moreover, although GDH1 deficiency resulted in decreased biosynthesis of lipids and RNA derived from glutamine, such changes in biosynthesis are dispensable to cancer cells when glucose dependent biosynthesis is predominant under normal, stress-free conditions. These metabolic changes are either advantageous (increased glycolysis) or dispensable (biosynthesis) to cancer cells. However, the GDH1 knockdown cells still showed decreased cell proliferation and tumor growth, indicating that other severe metabolic defects due to GDH1 deficiency eventually overshadow these changes. Experiments disclosed herein indicate that GDH1 regulates redox homeostasis through GPx1 which shed insights into the current understanding of the biological functions of GDH1 and reveal a distinct crosstalk between glutaminolysis and redox maintenance.

Targeting GDH1 with shRNA or a small molecule inhibitor R162 led to reduced cancer cell proliferation and tumor growth. Treatment with the cell permeable GDH1 product, methyl-a-KG, significantly rescued these phenotypes. However, rescue of alpha-KG level by methyl-alpha-KG significantly but not completely reversed decreased cell proliferation in GDH1 knockdown cells, suggesting that the effects of GDH1 on cell proliferation are dependent not only on enzyme activity but also on protein level.

In addition, antioxidant NAC treatment reversed ROS levels to that of control cells, but could not completely rescue the reduced cell proliferation or tumor growth in GDH1 knockdown cells. This suggests that GDH1 regulates not only redox status but also other cellular properties that contribute to the regulation of cancer cell proliferation and tumor growth. Experiments reported herein indicate that attenuation of GDH1, commonly upregulated in human cancers, specifically reduced breast cancer, lung cancer, and leukemia cell proliferation but not that of non-malignant human proliferating cells. Targeting GDH1 regulates both glutaminolysis and redox balance in cancer cells, suggesting GDH1 as an attractive anticancer target. Although the antioxidant polyphenol flavonoid, EGCG, is reported to inhibit GDH1 activity, it is a general inhibitor of NADPH-dependent enzymes. R162 has promising efficacy in inhibiting cancer cell proliferation as well as primary leukemia cells from patients with minimal cytotoxic effects to human cells. R162 also has promising efficacy in vivo with minimal toxicity. GDH1 could be a promising alternative therapeutic target for the clinical treatment of human cancers that rely heavily on glutamine metabolism.

Glutamate Dehydrogenase 1 Inhibitors

In certain embodiments, the disclosure contemplates methods of treating or preventing cancer comprising administering an effective amount of a glutamate dehydrogenase 1 inhibitor to a subject in need thereof. In certain embodiments, the GDH1 inhibitor has Formula I:

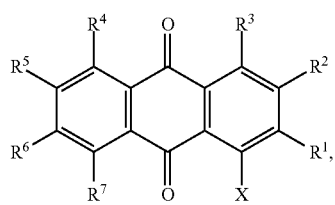

Formula I prodrugs, derivatives, or salts thereof wherein,

X is hydroxyl optionally substituted with $R^{10}$;

$R^1$ is $C_{1-6}$alkenyl, wherein $R^1$ is optionally substituted with one or more, the same or different, $R^{10}$;

$R^2$, $R^3$, $R^4$, $R^5$, $R^6$, and $R^7$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkanoyl, alkylsulfinyl, alkyl sulfonyl, aryl sulfonyl, benzyl, benzoyl, carbocyclyl, aryl, or heterocyclyl, wherein $R^2$, $R^3$, $R^4$, $R^5$, $R^6$, and $R^7$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkanoyl, alkylsulfinyl, alkylsulfonyl, arylsulfonyl, benzyl, benzoyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, benzyl, benzoyl, carbocyclyl, aryl, or heterocyclyl.

In certain embodiments, X is hydroxyl and $R^1$ is allyl.

In certain embodiments, the GDH1 inhibitor is 2-allyl-1-hydroxyanthracene-9,10-dione, prodrugs, derivatives, or salts thereof.

In certain embodiments, the GDH1 inhibitor is purpurin, derivative, or salt thereof.

In certain embodiments, the GDH1 inhibitor is epigallocatechin gallate, prodrugs, derivatives, or salts thereof.

RNA Interference

In certain embodiments, the GDH1 inhibitor is iRNA that targets GLUD1 mRNA. In certain embodiments, the GDH1 inhibitor is shRNA designed to knock down gene expression. RNA interference initially discovered in plants as Post-Transcriptional Gene Silencing (PTGS), is a highly conserved mechanism triggered by double-stranded RNA (dsRNA) and able to down regulate transcript of genes homologous to the dsRNA. The dsRNA is first processed by Dicer into short duplexes of 21-23 nt, called short interfering RNAs (siRNAs). Incorporated in RNA-induced silencing complex (RISC), they are able to mediate gene silencing through cleavage of the target mRNA.

"siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target and not directed to a mRNA poly A tail.

The length of the region of the siRNA complementary to the target, in accordance with the present disclosure, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer. In certain embodiments, the RNA capable of RNA interference comprises a human GDH1 sequence of 18 to 25 nucleotides or greater than 15, 16, 17, or 18 nucleotides. Human GDH1, transcript variant 1, mRNA mRNA sequence is ACCESSION NM_005271, hereby incorporated by reference. Alternatively spliced transcript variants encoding distinct isoforms have been found for this gene.

Xu et al. report enhancing tumor cell response to chemotherapy through nanoparticle-mediated co-delivery of siRNA and cisplatin prodrug. Proc Natl Acad Sci U S A. 2013, 110(46): 18638-43 .

He et al. report self-assembled nanoscale coordination polymers carrying siRNAs and cisplatin for effective treatment of resistant ovarian cancer. Biomaterials. 2015, 36:124-3.

Cho et al. report targeted delivery of siRNA-generating DNA nanocassettes using multifunctional nanoparticles. Small. 2013, 9(11):1964-73.

Since siRNA may be expressed from a RNA polymerase III (e.g., U6 or H1) promoter, a short hairpin siRNA (shRNA) gene may be cloned into expression vectors containing a polymerase III promoter to produce shRNAs from plasmid or viral vectors following transfecting into cells. See Brummelkamp et al., Science, 2002, 296, 550-553; Miyagishi & Taira, Nat. Biotechnol, 2002, 20, 497-500; McAnuff et al, J. Pharm. Sci. 2007, 96, 2922-2930; Bot et al., Blood, 2005, 106, 1147-1153. The shRNAs are further processed into siRNAs by a cellular endoribonuclease.

In certain embodiments, the disclosure relates to particles comprising a nucleic acid such as siRNA, DNA encoding for a siRNA, or siRNA expressing nanocassettes targeting GDH1. In certain embodiments the disclosure relates to the particle further comprising a targeting ligand, e.g., shRNA, and a ligand that targets a receptor specifically expressed on tumor cells. In certain embodiments, the nanoparticales can be lipid particles, liposomes, lipoplexes, lipoids, polymers particles, cyclodextrin particles, Chitosan particles, polyethylene particles, gold particles, quantum dots (QDs) or iron oxide nanoparticles (IONPs). The particle may carry a chemotherapy drug. See Lee et al. Biomed Res Int. 2013, 2013:782041 entitled recent developments in nanoparticle-based siRNA delivery for cancer therapy.

Methods of Use

This disclosure relates to methods of treating or preventing cancer comprising administering an effective amount of a glutamate dehydrogenase 1 inhibitor to a subject in need thereof. In certain embodiments, the disclosure relates to methods of treating or preventing cancer comprising administering a pharmaceutical composition comprising GDH1 inhibitors disclosed herein to a subject diagnosed with, exhibiting symptoms of, or at risk of cancer. In certain embodiments, the cancer is selected from the group consisting of leukemia, melanoma, cervical, ovarian, colon, breast, gastric, lung, skin, ovarian, pancreatic, prostate, head, neck, and renal cancer.

In certain embodiments, the pharmaceutical composition is administered in combination with a second chemotherapeutic agent such as, but not limited to, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

In certain embodiments, the disclosure relates to therapeutic methods disclosed herein wherein the pharmaceutical compositions are administered before, after or during radiotherapy.

In certain embodiments, the disclosure relates to uses of compounds disclosed herein in the production of a medicament for the treatment or prevention of cancer.

In certain embodiments, the disclosure contemplates methods of determining whether a compound is an inhibitor of GDH1 comprising mixing a test compound with GDH1 and glutamine or glutamate under conditions such that alpha-KG is formed and measuring the production of alpha-KG providing a test measurement and comparing the test measurement to a standard, normal, control, or reference measurement to indicate the amount of GDH1 inhibition in the presence of the test compound wherein a decrease of alpha-KG formation, or other associated products or rate associated therewith indicates an inhibition of GDH1 and wherein no change or an increase of alpha-KG formation, or other associated products or rate associated therewith indicates no inhibition or antagonism.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, esters, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. In certain embodiments, the compound is administered by inhalation through the lungs.

The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

In certain embodiments, the pharmaceutical composition comprises a compound disclosed herein and a propellant. In certain embodiments, an aerosolizing propellant is compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising a compound herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicon dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compound described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compound can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

EXPERIMENTAL

Enzyme Activity Assays

GDH1 enzyme activity assay was performed. Total cell lysates (20 microg) or 100 ng of purified GDH1 was added to a reaction mixture containing 50 mM triethanolamine (pH 8.0), 100 mM ammoniumacetate, 100 microM NADPH, and 2.6 mM EDTA. The reaction was initiated by adding alpha-KG, and the activity was assessed by monitoring the oxidation of NADPH as a decrease in absorbance at 340 nm. GPx, SOD, TRX, GSR, and CAT enzyme activities were determined by using commercially available kits from Biovision according to the manufacturer's instructions. PRX enzyme activity was assayed by coupling its activity to oxidation of NADPH via TRXs.

Glutaminolysis Rate Measurement

Glutamine oxidation assay measuring $^{14}CO_2$ from $^{14}C$ glutamine was used to determine glutaminolysis rate. Cells were seeded on 6-cm dishes that were placed in a sealed 10-cm dish. Cells were incubated with 4 mCi/ml of [U—$^{14}C$] glutamine for 4 hr, and the reaction was stopped by the addition of 200 ml of 70% perchloric acid, which also released $CO_2$; 0.5 ml of 3 M NaOH was injected to a cup placed next to the 6-cm dish to absorb all the released $CO_2$ from the cells and after 12 hr incubation and 20 ml of NaOH was subjected to liquid scintillation counting.

Radiometric $^{14}C$-Fumarate/$^{14}C$-alpha-KG-GPx1 Binding Assay

Bead-bound flag-GPx1 purified from transfected 293T cell lysates was washed with Tris-buffered saline (TBS) buffer (50 mM Tris, 150 mM NaCl [pH 7.5]), followed by incubation with 0.12 microCi $^{14}C$-fumarate or $^{14}C$-alpha-KG for 30 min in TBS buffer. The beads were then washed with TBS buffer. The bead-bound GPx1 protein was eluted with 10 microg flag peptides, and radioactivity was detected by liquid scintillation counting.

Cell Proliferation Assay

Adherent cells or leukemia cells were seeded in six-well plate, and cell numbers were determined by trypan blue exclusion using TC10 automated cell counter (Bio-Rad). For alpha-KG, NAC, and R162 treatment experiments, cells were treated with different concentrations of alpha-KG, NAC, and R162, followed by cell counting.

RNA Interference

Lentivirus production, cell infection for RNAi and protein overexpression in human cells and stable cell selection are described in Jin et al., 2013 Mol. Cell. Biol. 33, 2574-2585. GLUD1 shRNA Plasmid is a target-specific lentiviral vector plasmid encoding a 19-25 nt (plus hairpin) shRNA designed to knock down gene expression. To knock down endogenous human genes, one generates lentiviruses carrying shRNA by transfecting 293T cells with lentiviral vectors encoding shRNA, pHRCMV8.2ΔR, and cytomegalovirus-vesicular stomatitis virus G protein (CMV-VSVG). One infects cells with the harvested lentivirus for 48 h or selects by using 2 μg/mL of puromycin for 1 week for stable selection.

Xenograft Studies

Nude mice (athymic nu/nu, female, 4-6 weeks old; Harlan) were subcutaneously injected with H1299 cells harboring empty vector on the left flank, and cells with stable knockdown of GDH1 on the right flank, respectively. For the NAC rescue experiment, mice of the NAC rescue group were treated with NAC drinking water at 10 mg/ml from 3 days after H1299-GDH1 shRNA cells injection for 42 days. To evaluate the efficacy of R162, the drug was administered from a day after H1299 cells injection by daily intraperitoneal injection of 30 mg/kg for 35 days. Fifty percent of DMSO in PBS was as a diluent control. Tumor growth was recorded by measurement of two perpendicular diameters of the tumors, and tumor size was calculated. The tumors were harvested and weighed at the experimental endpoint. Tumor proliferation was determined by Ki-67 IHC staining.

Figure 1B:
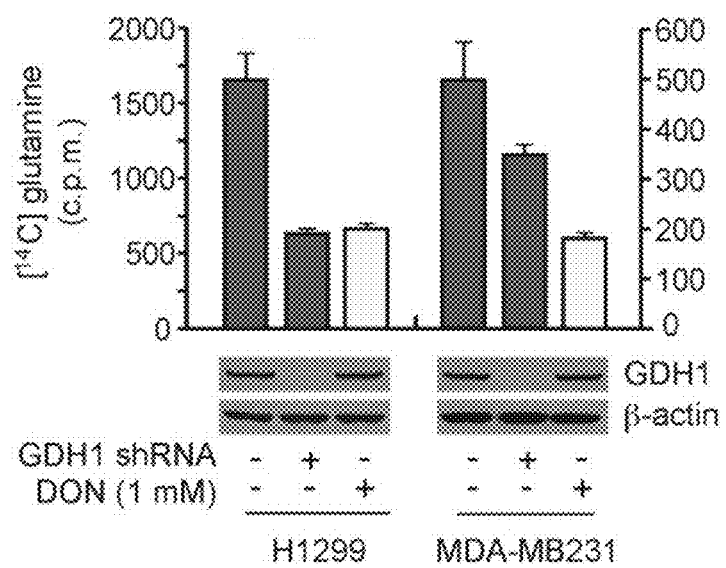
FIG. 1B shows data on glutaminolytic rates in H1299 and MDA-MB231 cells determined with stable knockdown of GDH1 or control cells harboring an empty vector. DON (6-diazo-5-oxo-I-norleucine), glutamine antagonist, was used as a positive control. GDH1 expression is shown by western blotting.
Figure 1C:
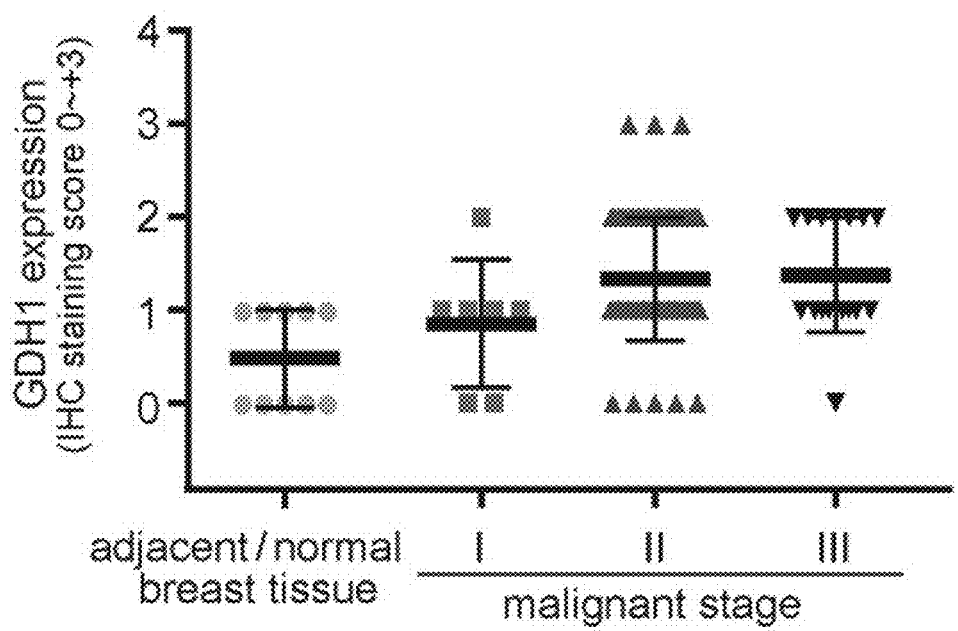
FIG. 1C shows data on immunohistochemistry analyses of GDH1 expression in groups of primary human tissue specimens for breast ductal carcinoma.
Figure 1D:
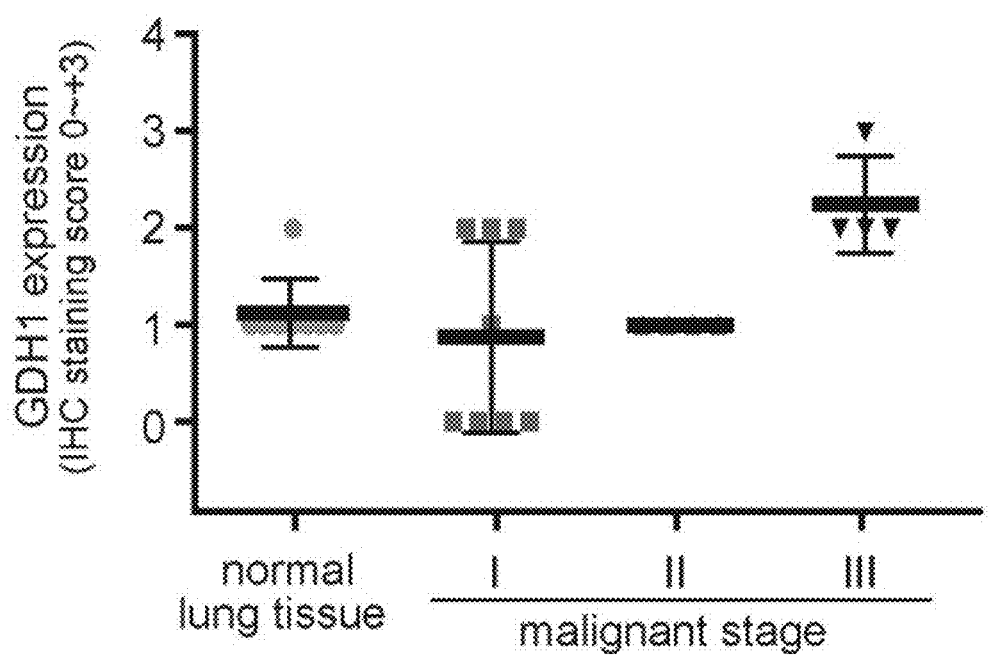
FIG. 1D shows data on immunohistochemistry analyses of GDH1 expression in groups of primary human tissue specimens for lung cancer.

GDH1 Predominantly Regulates Alpha-KG Production in Cancer Cells and is Upregulated in Human Cancers The effect of blocking the conversion of glutamate to alpha-KG was tested on cancer cells. Experiments indicate that GDH1 is the enzyme predominantly responsible for the conversion of glutamate to alpha-KG compared with the other two mitochondrial enzymes, GOT2 and GPT2, in lung cancer H1299 cells and breast cancer MDA-MB231 cells (FIG. 1A). Moreover, shRNA-mediated stable knockdown of GDH1 resulted in a significantly attenuated glutaminolysis rate compared with that in control cells harboring an empty vector (FIG. 1B), suggesting a role of GDH1 in glutaminolysis in human cancer cells. Furthermore, GDH1 expression levels correlate with progressive stages of breast cancer and lung cancer as was demonstrated by performing immunohistochemical staining (IHC) using primary tissue microarray samples from breast and lung cancer patients (FIGS. 1C and 1D, respectively). GDH1 expression levels were significantly increased in the tumor samples from patients with advanced stages of breast or lung cancer compared with adjacent normal tissues from the same patients or normal tissues from individuals with no cancer.

GDH1 is Important for Cancer Cell Proliferation and Tumor Growth

Figure 2A:
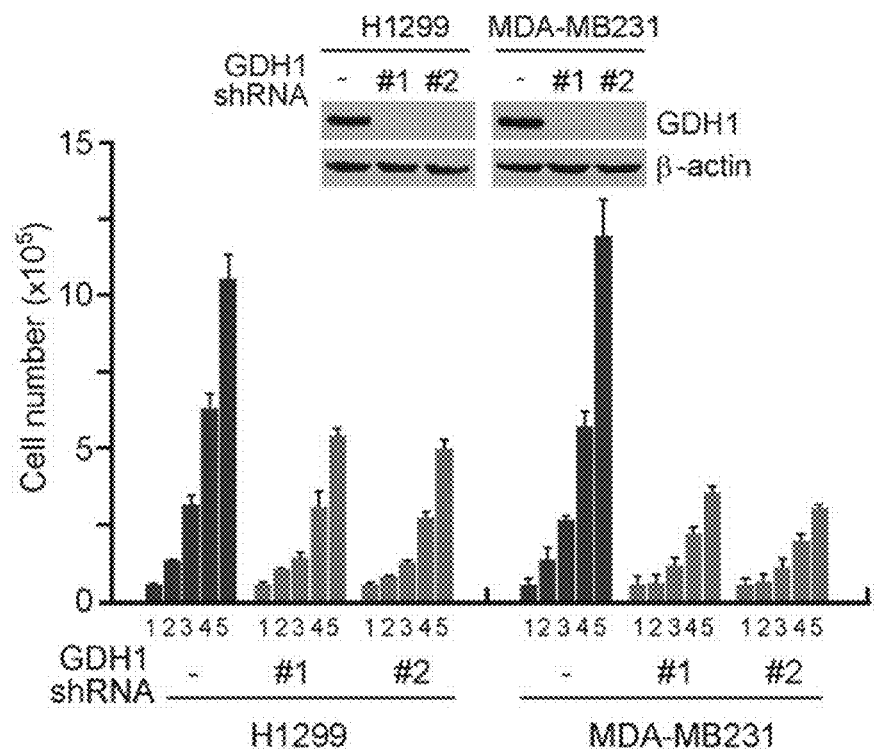
FIG. 2A shows data indicating GDH1 is important for cancer cell proliferation and tumor growth. Data on H1299 lung cancer and MDA-MB231 breast cancer cells. Cell proliferation rates were determined by cell counting in H1299 and MDA-MB231 tumor cells with stable knockdown of GDH1 compared with control cells expressing an empty vector. Expression of GDH1 in cells transduced with GDH1 shRNA clones is shown by western blot analyses.
Figure 2B:
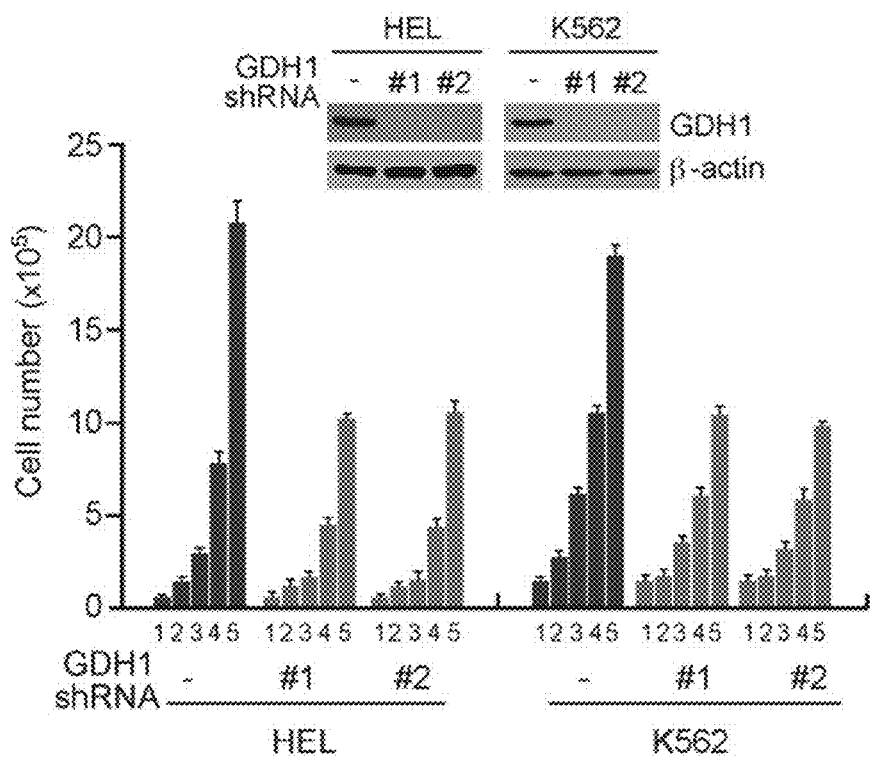
FIG. 2B shows data on HEL and K562 leukemia cells.
Figure 2C:
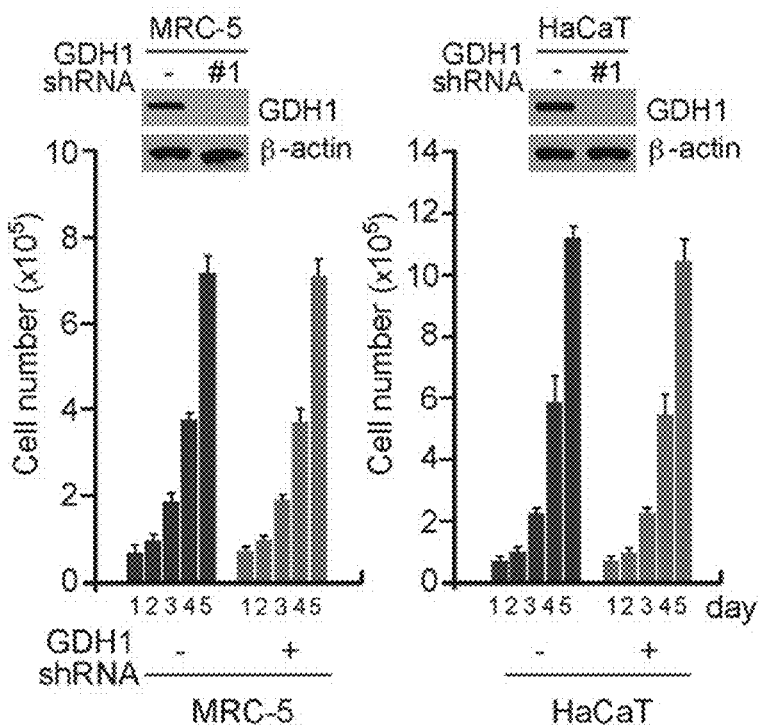
FIG. 2C shows data on MRC-5 and HaCaT cells.
Figure 2D:
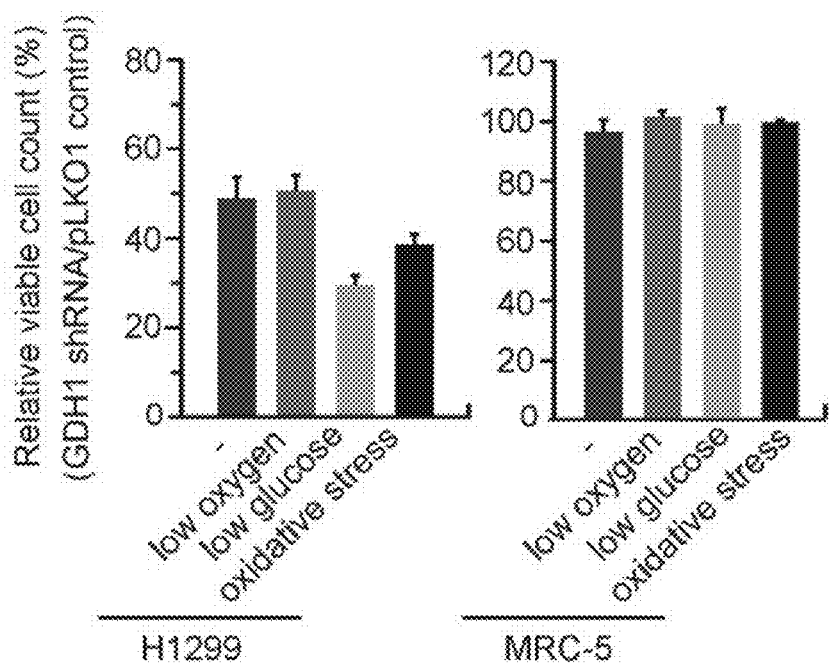
FIG. 2D shows data on GDH1 knockdown and cell proliferation rates measured under stress conditions, including low oxygen (1% $O_2$), low glucose (0.5 mM glucose), and oxidative stress (15 mM $H_2O_2$).
Figure 2E:
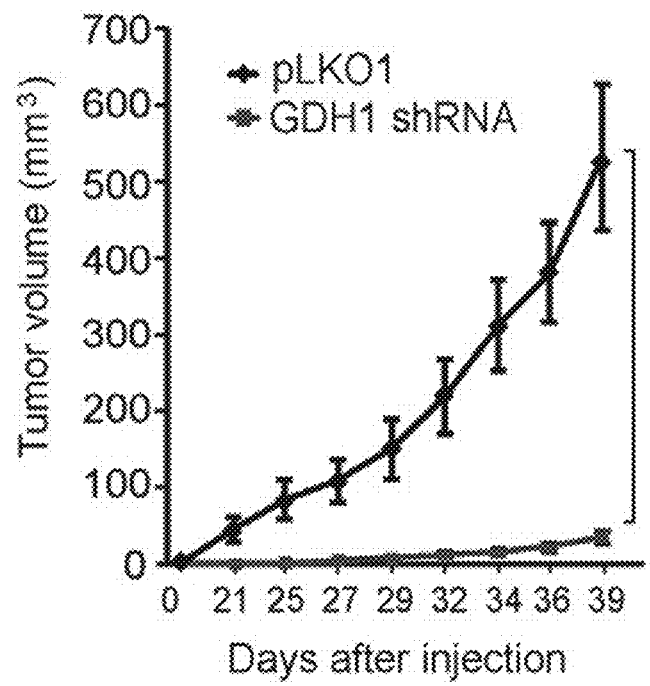
FIG. 2E shows data on GDH1 knockdown and tumor growth potential of H1299 cell xenograft mice. Tumor size was monitored every 2-3 days for 6 weeks.
Figure 2F:
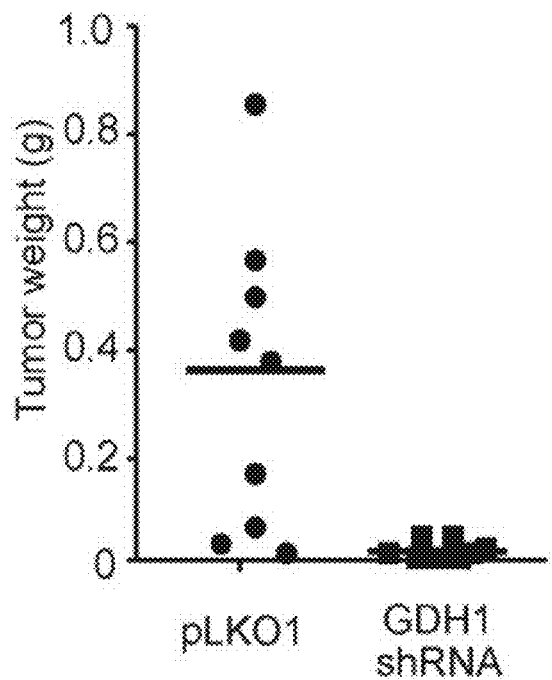
FIG. 2F shows data on tumor weights that were examined at the experimental endpoint.

A group of human cancer cell lines with stable knockdown of GDH1 were generated. These included H1299 and MDA-MB231 tumor cells (FIG. 2A), as well as human leukemia HEL and K562 cells (FIG. 2B). Nonmalignant, proliferating human fetal lung fibroblast MRC-5 and human keratinocyte HaCaT were included as controls. Stable knockdown of GDH1 resulted in decreased cell number in all of the cancer cell lines tested, but not in control normal proliferating cells (FIG. 2C), suggesting a crucial role of GDH1 in cancer cell proliferation. Similar results were obtained from colony formation assay and DNA-based cell proliferation assay. Oxidative stress and low glucose culture conditions but not hypoxic conditions further attenuated cell proliferation upon GDH1 knockdown in H1299 lung cancer cells (FIG. 2D). Moreover, a xenograft experiment was performed in which nude mice were subcutaneously injected with H1299 cells harboring an empty vector and H1299 cells with GDH1 knockdown grown on the left and right flanks, respectively. The GDH1 knockdown resulted in significantly reduced tumor growth in most of the mice, with four of nine mice tumor free compared with tumors derived from control cells with empty vector (FIGS. 2E, 2F). These results together suggest that GDH1 confers a proliferative advantage to cancer cells and tumor growth.

GDH1 is Critical for Redox Regulation, but not Bioenergetics or Anabolic Biosynthesis, in Cancer Cells A set of metabolic assays was performed using lung cancer H1299 and breast cancer MDA-MB231 cells with GDH1 knockdown (shRNA). Attenuation of GDH1 in cancer cells did not affect the intracellular ATP levels compared with control cells harboring an empty vector. GDH1 knockdown cells showed increased glucose uptake, glycolytic rates, and lactate production but unaltered oxygen consumption rate compared with control cells. In addition, intracellular ATP levels were significantly decreased in GDH1 knockdown cells compared with control cells upon treatment with glycolytic inhibitor, 2-deoxyglucose (2-DG), or glucose deprivation, but not when treated with oligomycin, an inhibitor of oxidative phosphorylation. These data together suggest that defective glutaminolysis due to GDH1 knockdown allows cells to further rely on glucose catabolism for bioenergetics. Moreover, GDH1 knockdown did not affect oxidative pentose phosphate pathway (PPP) flux or the overall lipid or RNA biosynthesis. However, knockdown of GDH1 significantly decreased glutamine-dependent RNA biosynthesis, whereas such change of RNA synthesis was not comparable to glucose-derived RNA synthesis. In contrast, GDH1 knockdown significantly attenuated intracellular ATP levels as well as overall lipid and RNA synthesis levels in cells under stress conditions, including low oxygen or low glucose suggesting that GDH1 is important in compensating glucose catabolism and oxidation in cells under stress. Nevertheless, since cells with GDH1 knockdown demonstrate reduced cell proliferation and tumor growth under normal conditions, it was hypothesized that other metabolic defects such as redox metabolism changes might be responsible for the proliferative disadvantage in cells conferred by GDH1 knockdown.

Figure 3A:
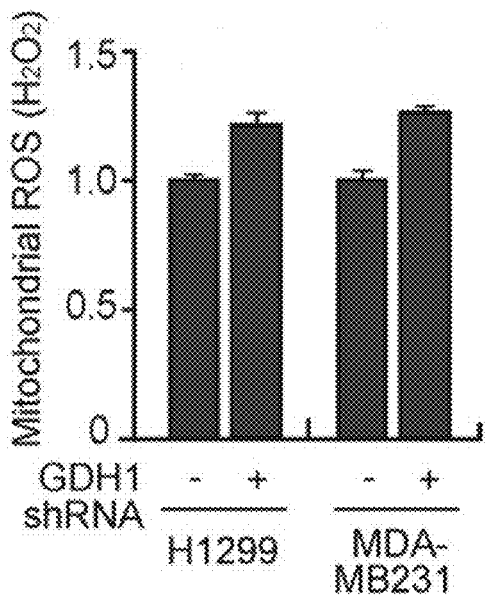
FIG. 3A shows data of mitochondrial ROS indicating GDH1 contributes to redox homeostasis in cancer cells.
Figure 3B:
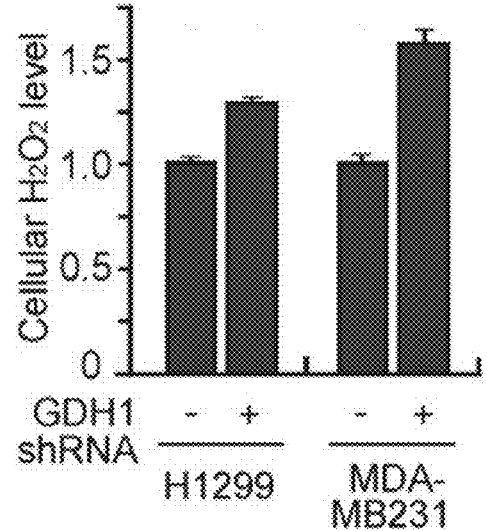
FIG. 3B shows data for cellular $H_2O_2$ levels.
Figure 3C:
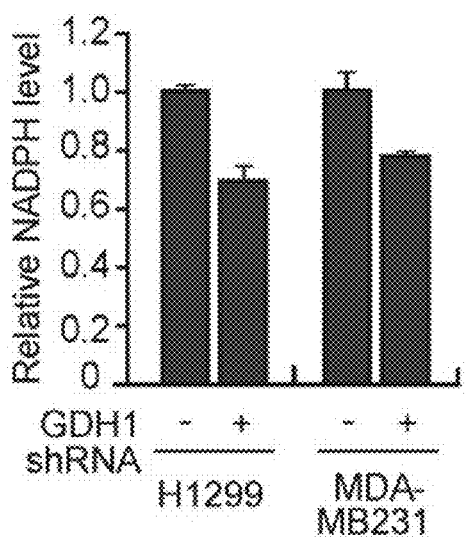
FIG. 3C shows data on NADPH levels determined in H1299 and MDA-MB231 cells with GDH1 knockdown or control cells with an empty vector.
Figure 3D:
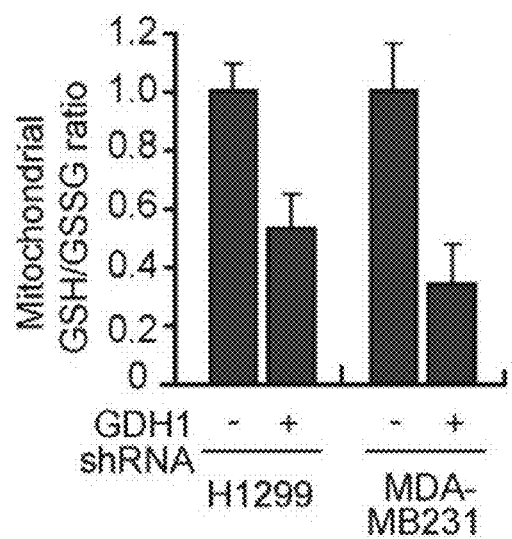
FIG. 3D shows data for mitochondrial GSH/GSSG ratio.
Figure 3E:
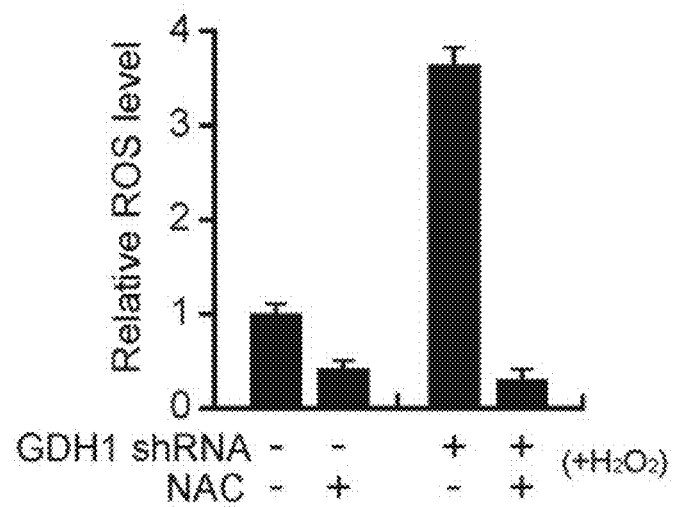
FIG. 3E shows data for ROS in H1299 cells with GDH1 knockdown treated with antioxidant agent NAC (1 mM).
Figure 3F:
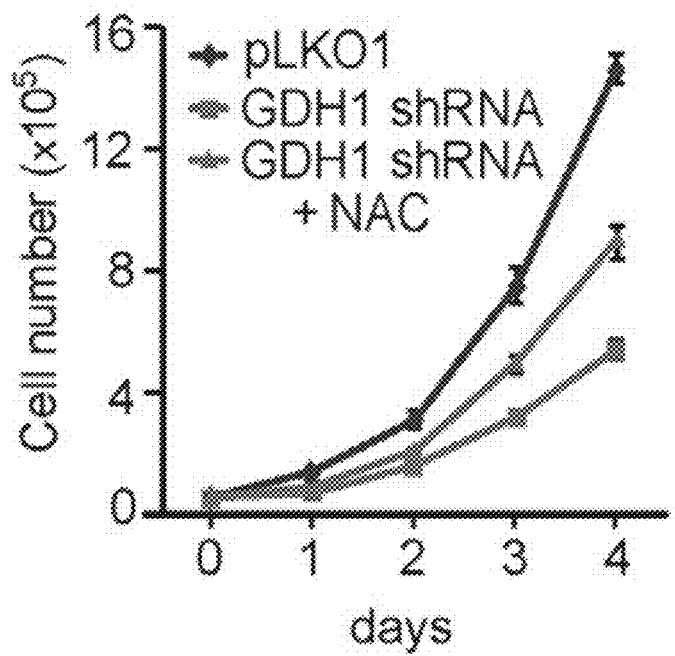
FIG. 3F shows data for cell proliferation.

Indeed, knockdown of GDH1 resulted in increased mitochondrial ROS levels (FIG. 3A) and intracellular $H_2O_2$ levels (FIG. 3B), while stress conditions induced by $H_2O_2$ or glucose deprivation resulted in further elevated ROS levels in GDH1 knockdown cells. In contrast, NADPH levels (FIG. 3C) and the GSH/GSSG ratio (FIG. 3D) were significantly decreased in GDH1 knockdown cells compared with control cells. These data together indicate that GDH1 is important for redox homeostasis in cancer cells, most likely by regulating ROS levels. Consistently, treatment with antioxidant N-acetylcysteine (NAC) in GDH1 knockdown cells significantly rescued the increased ROS and reduced cell proliferation due to GDH1 deficiency (FIG. 3E and FIG. 3F).

Figure 3G:
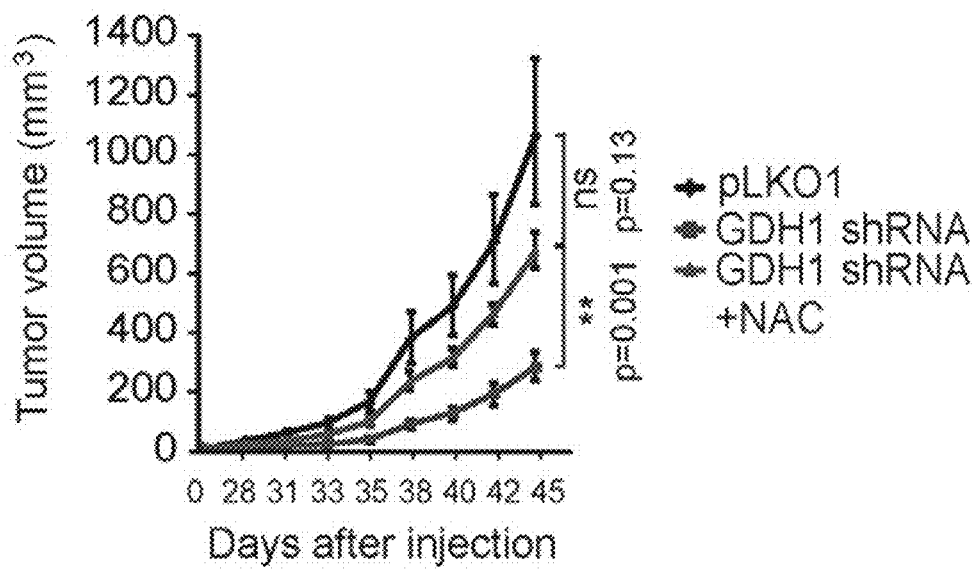
FIG. 3G shows data when NAC (10 mg/ml drinking water) was administered in H1299 xenograft mice with GDH1 knockdown. Tumor growth was monitored.
Figure 3H:
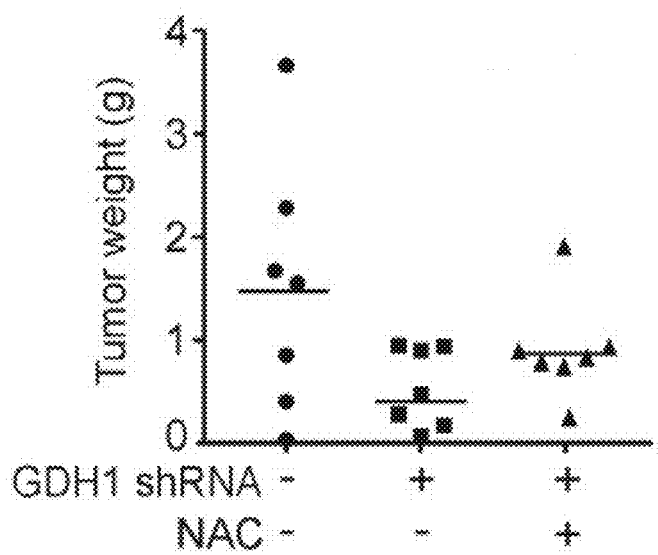
FIG. 3H shows data on tumor weights examined at the experimental endpoint.

Next, this was functionally validated in vivo by performing xenograft experiments. Nude mice were subcutaneously injected with control H1299 cells harboring empty vector or GDH1 knockdown cells. NAC at a concentration of 10 mg/ml was administered via drinking water to half of the mice injected with GDH1 knockdown cells. NAC treatment partially rescued the attenuated tumor growth of H1299 GDH1 knockdown cells in xenograft nude mice (FIGS. 3G, 3H). To determine whether GDH1 enzyme activity is important for ROS regulation, tests were performed to determine whether rescue of reduced intracellular levels of the GDH1 product, alpha-KG, could reverse the elevated ROS level in GDH1 knockdown cells (FIGS. 3I, 3J, 3K). Indeed, cell-permeable methyl-a-KG significantly rescued the attenuated intracellular alpha-KG (FIG. 3I), elevated ROS (FIG. 3J), and decreased cell proliferation (FIG. 3K) levels in GDH1 knockdown cells. These data suggest that GDH1 requires its enzyme activity to regulate ROS, which contributes to redox homeostasis and cancer cell proliferation.

Figure 4A:
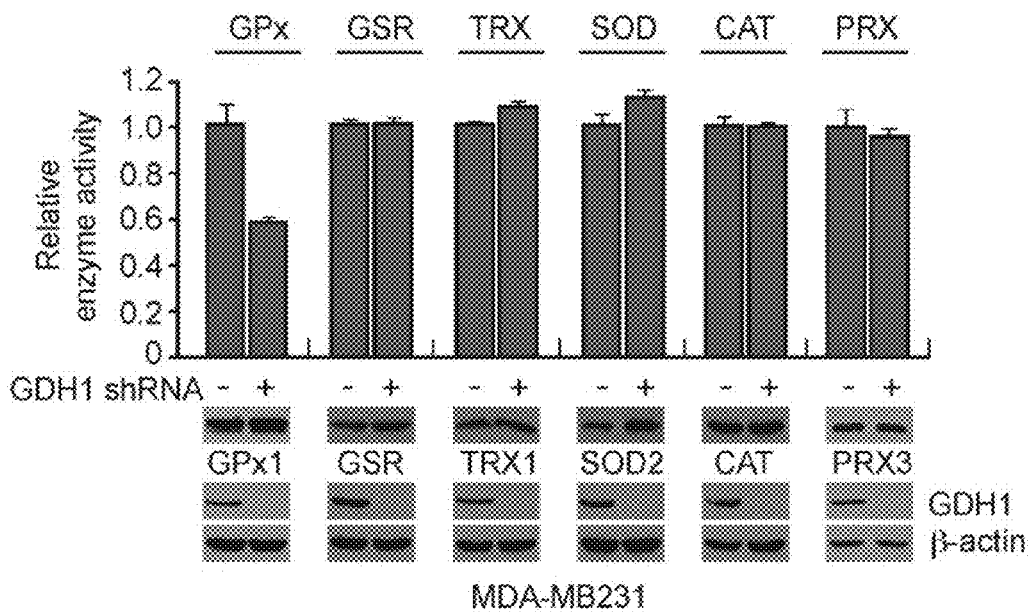
FIG. 4A shows data indicating GDH1 contributes to redox homeostasis in part by regulating GPx activity in cancer cells. Effect of GDH1 knockdown on the enzyme activity of GPx and other ROS scavenging enzymes, including GSR, TRX, SOD, CAT, and PRX in MDA-MB231. Western blots displaying the expression of GPx1, GSR, TRX1, SOD2, CAT, PRX3, and GDH1 in cells with GDH1 stable knockdown or an empty vector. Beta-actin was used as a loading control.
Figure 4B:
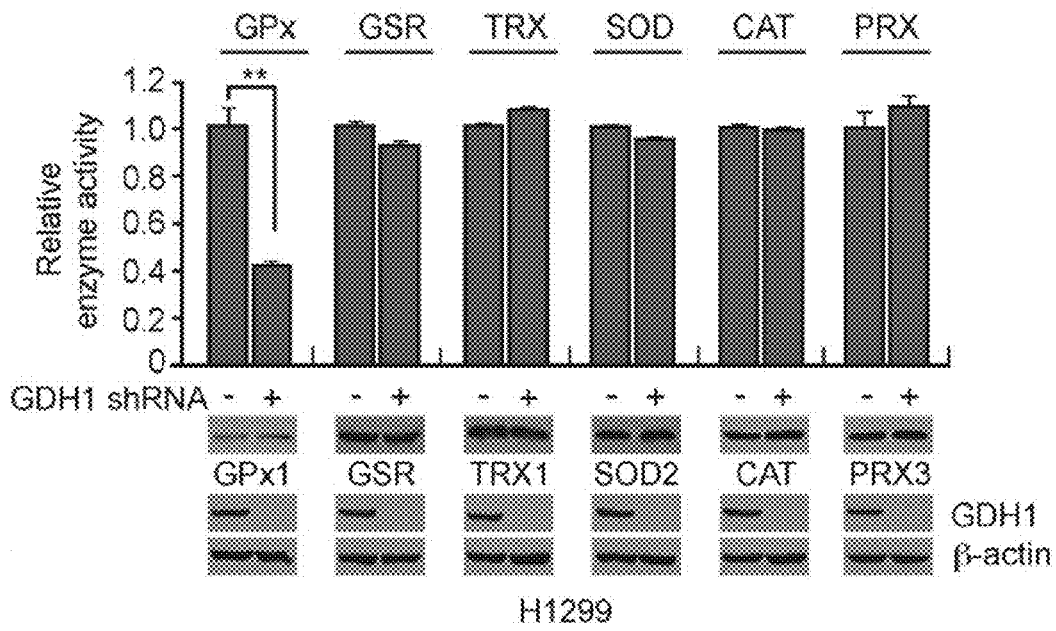
FIG. 4B shows data in H1299.
Figure 4C:
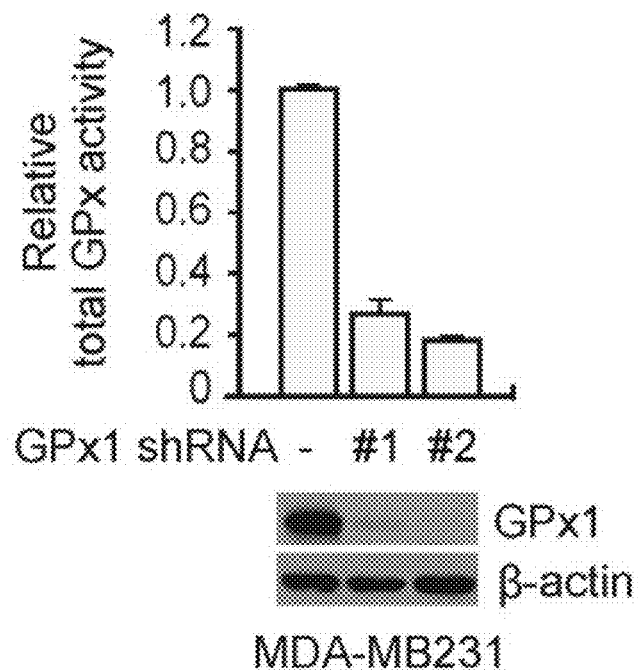
FIG. 4C shows data on GPx1 knockdown and total GPx activity, in MDA-MB231 cancer cells. Knockdown efficiency of GPx1 was determined by western blotting. Cell proliferation rates and ROS levels were assessed by cell counting and carboxy-H2DCFDA detection.
Figure 4D:
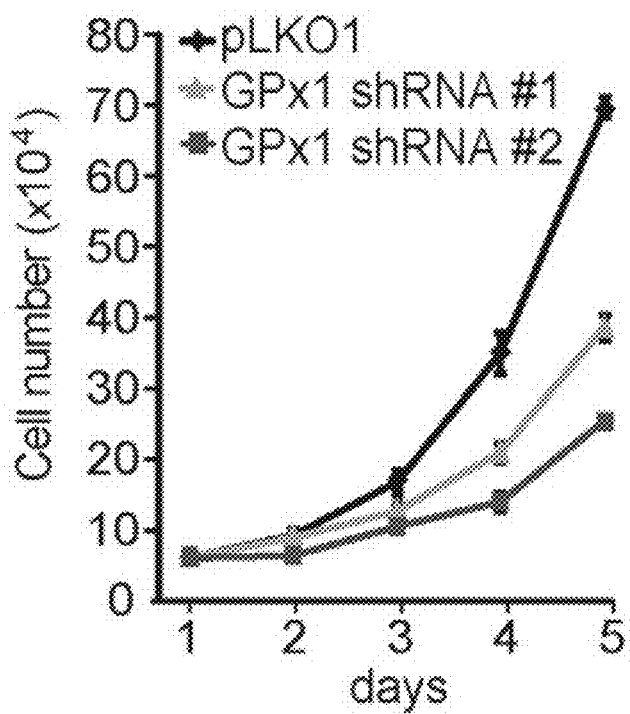
FIG. 4D shows data for cell proliferation.
Figure 4E:
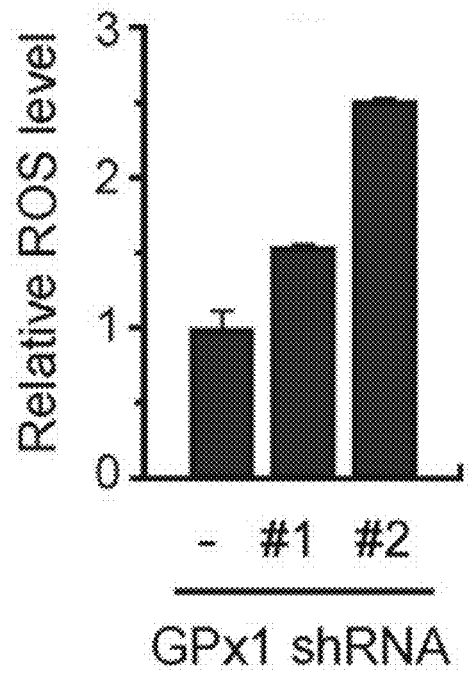
FIG. 4E shows data for ROS.
Figure 4F:
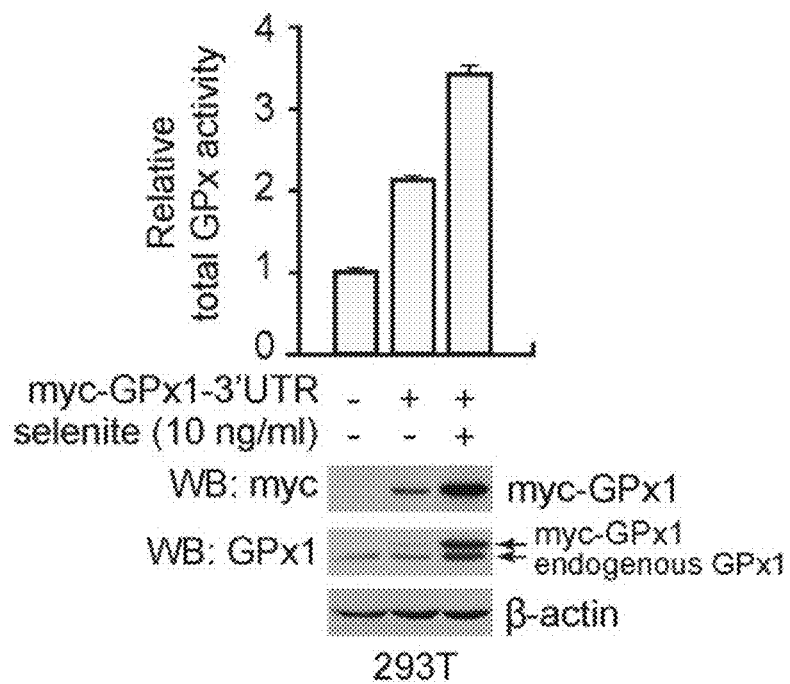
FIG. 4F shows data when GPx1 expression in 293T cells is transduced with a GPx1 expression construct harboring a 3'UTR with a SECIS element that responds to selenite. Expression of myc tagged GPx1 was determined by immunoblotting using anti-myc and anti-GPx1 antibodies.
Figure 4G:
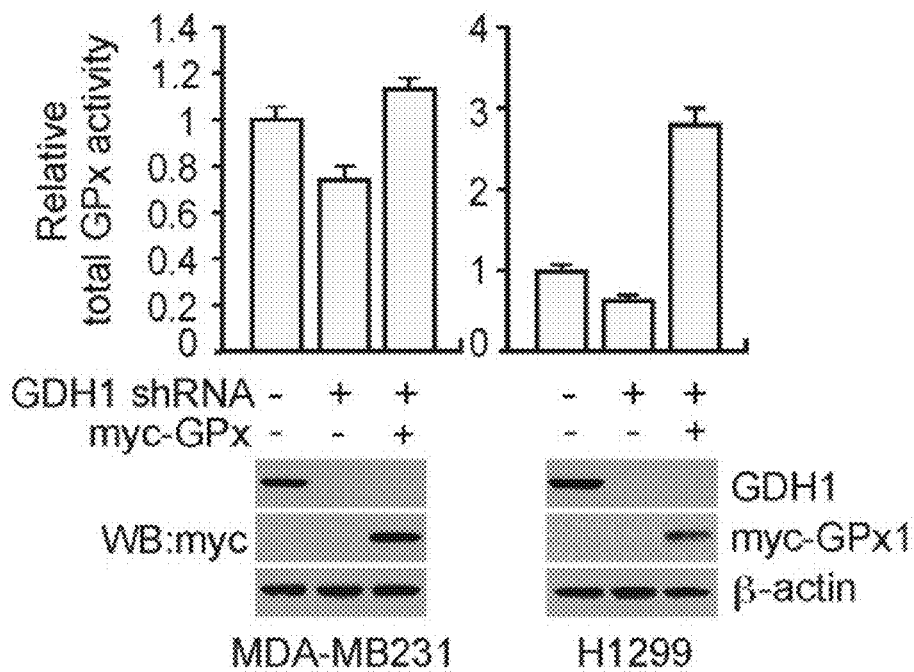
FIG. 4G shows data on myc-GPx1 stable expression and the total cellular GPx activity, in MDA-MB231 and H1299 cells with stable knockdown of GDH1. Ten ng/ml selenite was added in the culture media for all the assays. GDH1 knockdown and myc-GPx1 expression is shown by western blot analyses.
Figure 4H:
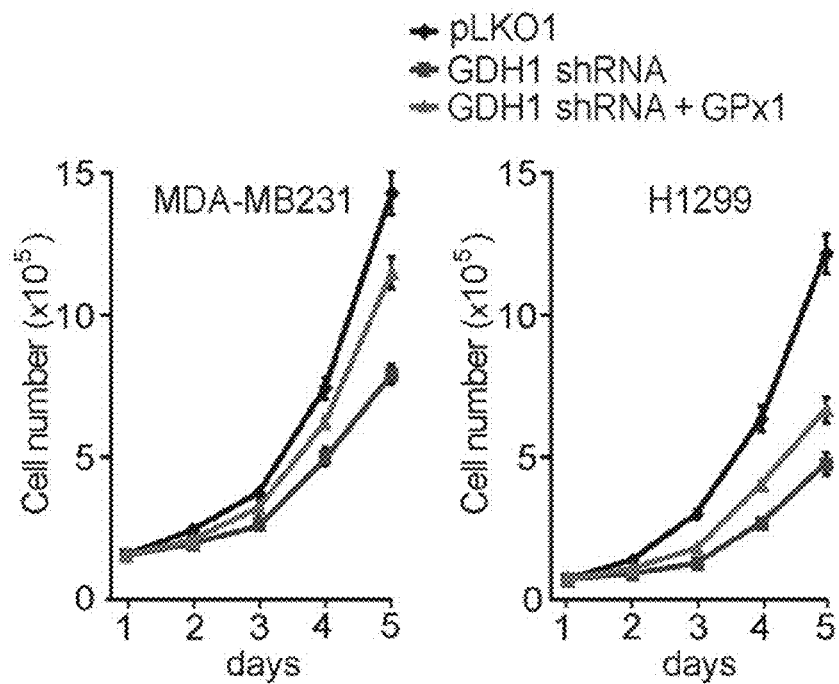
FIG. 4H shows data for cell proliferation.
Figure 4I:
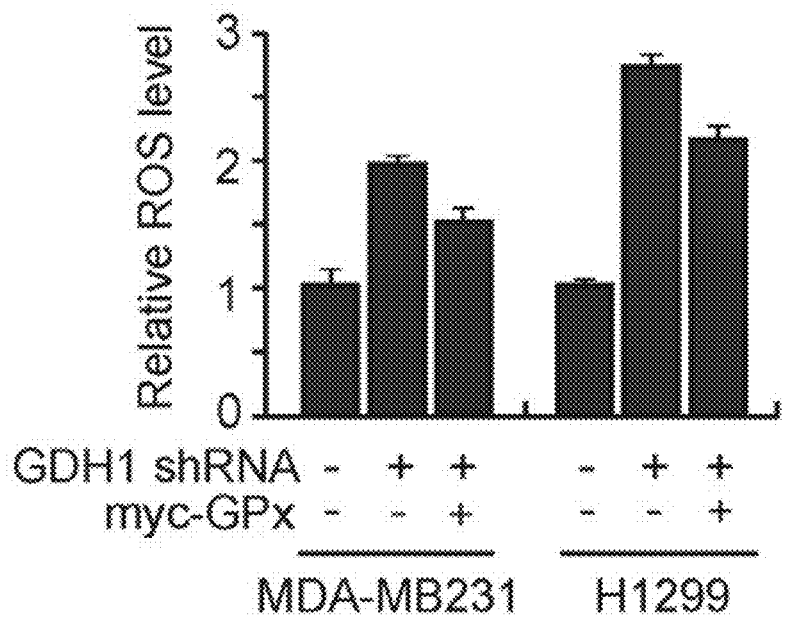
FIG. 4I shows data for ROS.

GDH1 Contributes to Redox Homeostasis in Part by Regulating GPx Activity in Cancer Cells To investigate how GDH1 regulates ROS levels in cancer cells, experiments were performed to test whether GDH1 knockdown attenuates any of the known ROS scavenging enzymes, including GPx, GSR, thioredoxin reductase (TRX), SOD, CAT, and PRX. Tests indicate that only GPx enzyme activity is significantly attenuated in GDH1 knockdown MDA-MB231 cells compared with control cells harboring an empty vector (FIG. 4A). Similar results were obtained using lung cancer H1299 cells (FIG. 4B). To further substantiate that GDH1 controls ROS levels through GPx in cancer cells, the effect targeting GPx on cell proliferation and ROS level of cancer cells were tested. Although GPx1, GPx3, GPx4, GPx6, and GPx8 exist in human breast cancer cell line MDA-MB231, GPx1 is the predominant isoform that contributes to GPx activity in cancer cells. Therefore, the impact of targeting GPx1 was assessed. RNAi-mediated downregulation of GPx1 effectively decreased total GPx activity (FIG. 4C). Moreover, knockdown of GPx1 mimicked the effect of GDH1 knockdown, leading to decreased cell proliferation and increased ROS (FIG. 4D, 4E). Whether overexpression of active GPx1 can reverse the increased ROS levels and attenuated cell viability in GDH1 knockdown cells was tested. GPx1 is a selenoprotein, which requires a selenocysteine insertion sequence (SECIS) element to translate the UGA codon in the GPx1 gene as selenocysteine (Walczak et al., 1998). A GPx1 construct with a 3'UTR containing the SECIS element to express GPx1 in cells were generated (FIG. 4F). Stable overexpression of active GPx1 rescued the attenuated total GPx activity in GDH1 knockdown cells, leading to increased proliferative ability and decreased ROS compared with control GDH1 knockdown cells (FIG. 4G, 4H, 4I). It was found that GPx1 co-localizes with GDH1 in the mitochondria and GDH1 regulates GPx1 activity in the mitochondria of cancer cells.

GDH1 Controls Fumarate Level to Potentiate GPx Activity

Figure 5A:
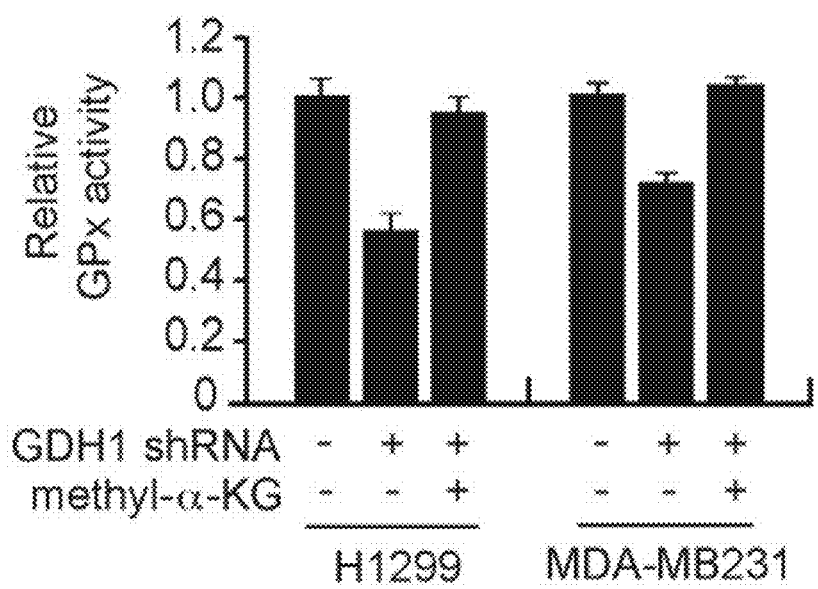
FIG. 5A shows data indicating GDH1 promotes GPx activity by controlling intracellular alpha-KG levels. GPx activity in cancer cells with stable knockdown of GDH1 was determined in the presence or absence of cell-permeable methyl-alpha-KG.
Figure 5B:
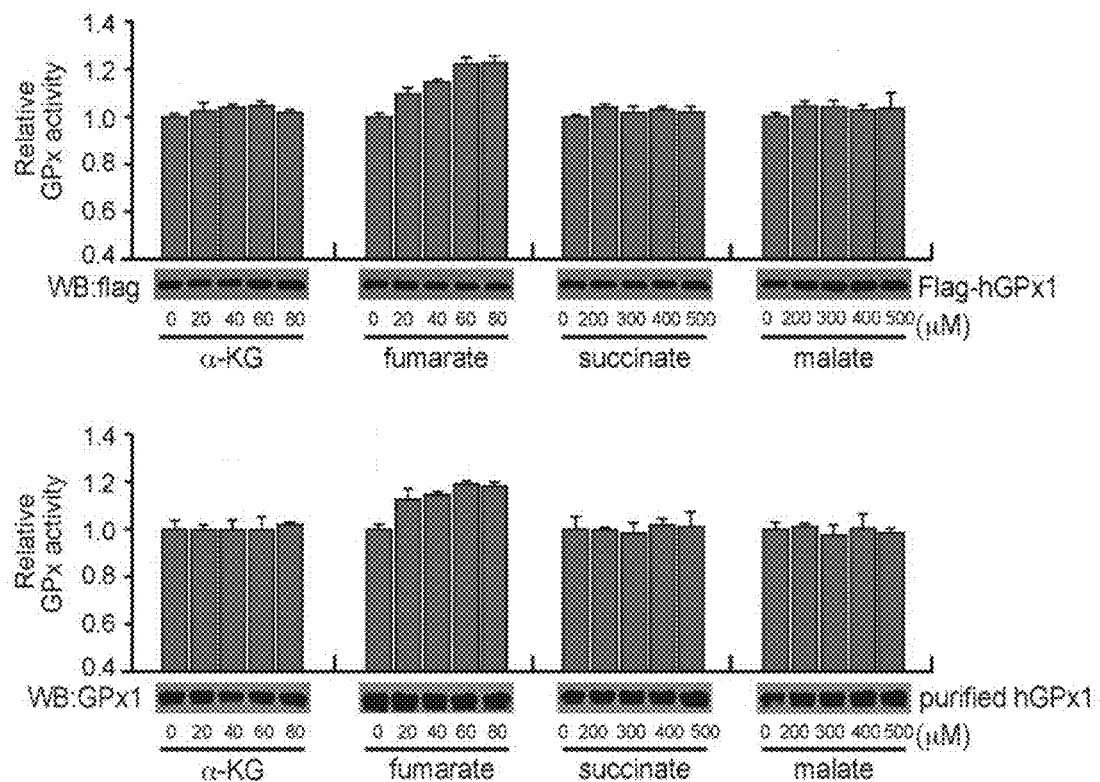
FIG. 5B shows data when purified flag-GPx1 from 293T cells or endogenous GPx1 from human erythrocytes were examined in the presence of increasing concentrations of alpha-KG, fumarate, succinate, or malate. Western blot analyses show GPx1 input for each sample.
Figure 5C:
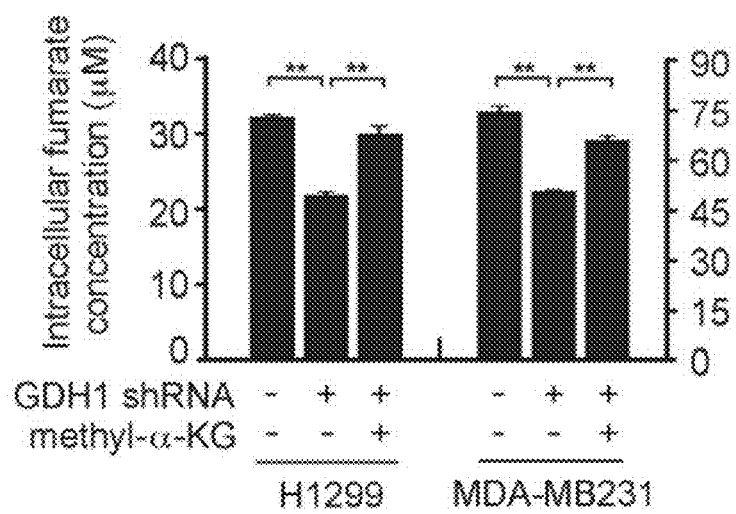
FIG. 5C shows data on the effects of methyl-alpha-KG treatment on intracellular fumarate level in GDH1 knockdown cells.

The molecular mechanism by which GDH1 regulates GPx activity was explored. Tests indicate that GDH1 does not form a protein complex with GPx1. It is hypothesized that GDH1 may indirectly regulate GPx activity and subsequent ROS levels by controlling intracellular levels of alpha-KG. As shown in FIG. 5A, treatment with methyl-alpha-KG fully rescued the attenuated GPx activity in GDH1 knockdown cells. Next, we incubated purified active GPx1 with physiological concentrations of alpha-KG (20-80 microM) or other metabolite intermediates derived from alpha-KG including fumarate (20-80 microM), succinate (200-500 microM), and malate (200-500 microM) to check whether these metabolites directly affect GPx1 activity in vitro (FIG. 5B), since each of these metabolites was significantly decreased in cancer cells upon GDH1 knockdown (FIGS. 1A, 5C,). Interestingly, activity of purified human GPx1 either from transient expression in mammalian cells (FIG. 5B, upper) or human erythrocytes (FIG. 5B, lower) was significantly increased in vitro by fumarate but not the other metabolites. Moreover, treatment with the GDH1 product methyl-alpha-KG rescued the decreased fumarate in cancer cells suggesting that GDH1 and its product, alpha-KG, control intracellular fumarate levels (FIG. 5C).

Figure 5D:
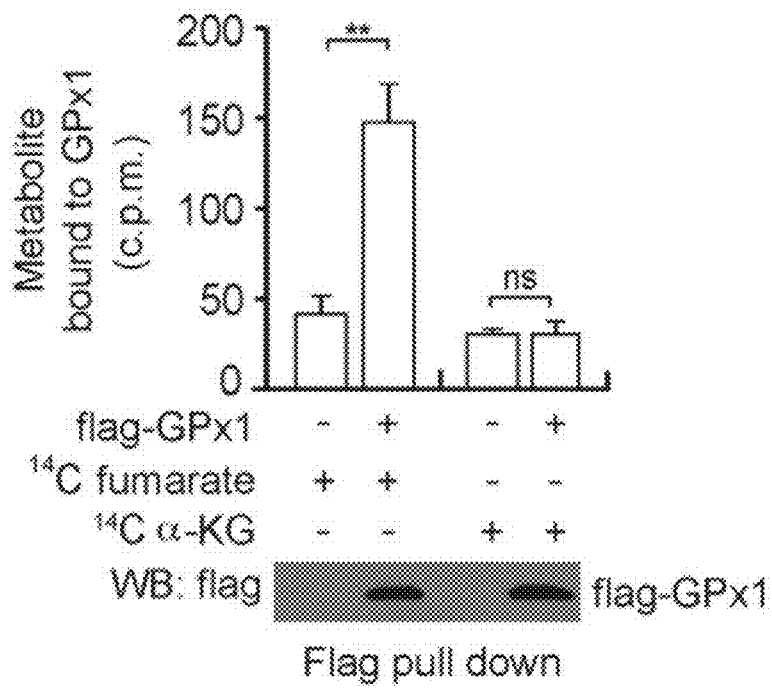
FIG. 5D shows data when Flag-GPx1 was pulled down from transfected 293T cell lysates and incubated with $^{14}$C-fumarate or $^{14}$C-alpha-KG. The unbound metabolites were washed away and retained fumarate or alpha-KG was measured using a scintillation counter. Western blot analysis shows GPx1 input for each sample.
Figure 5E:
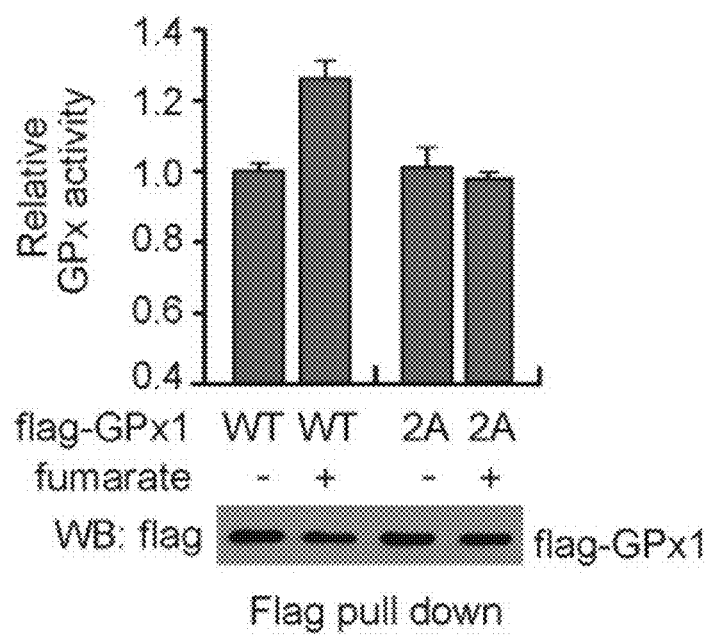
FIG. 5E shows data on the activity of purified flag-GPx1 WT or fumarate binding-deficient mutant flag-GPx1 T143A/D144A (2A) from 293T cells in the presence of fumarate (80 microM). Western blot analysis shows GPx1 input for each sample.
Figure 5F:
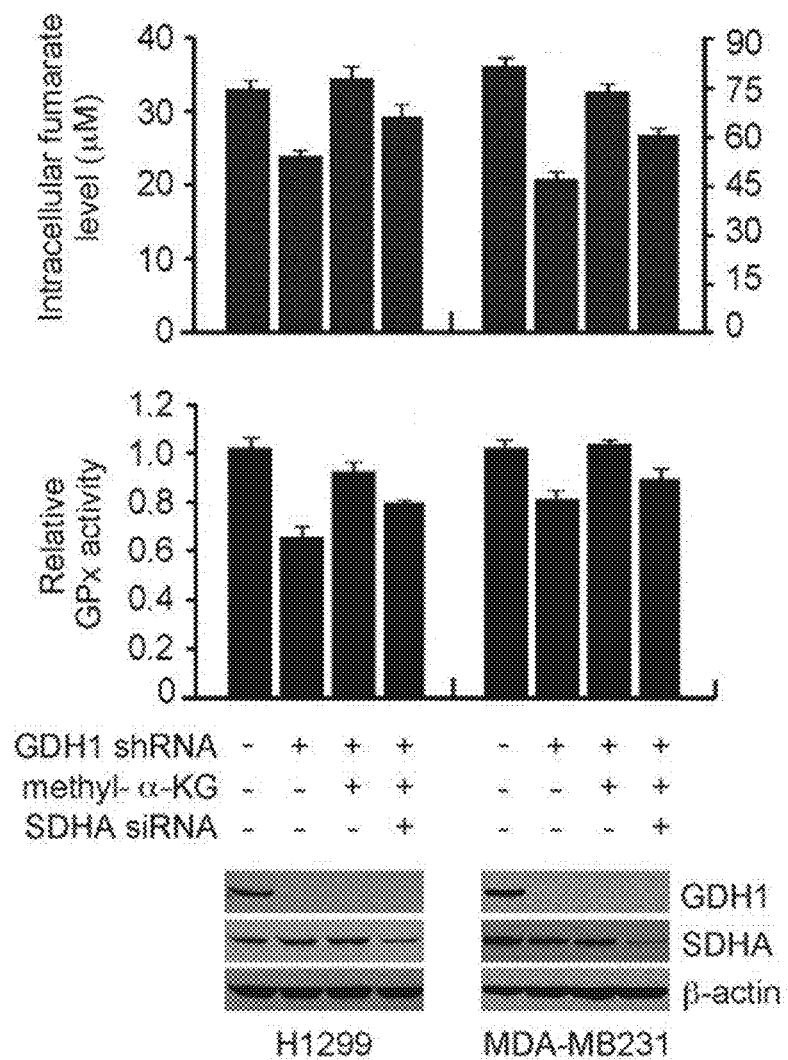
FIG. 5F shows data on the intracellular fumarate levels and relative enzyme activity of endogenous GPx in GDH1 knockdown cells determined in the presence or absence of methyl-alpha-KG and SDHA siRNA. Knockdown of GDH1 and SDHA is shown by western blot analyses.
Figure 5G:
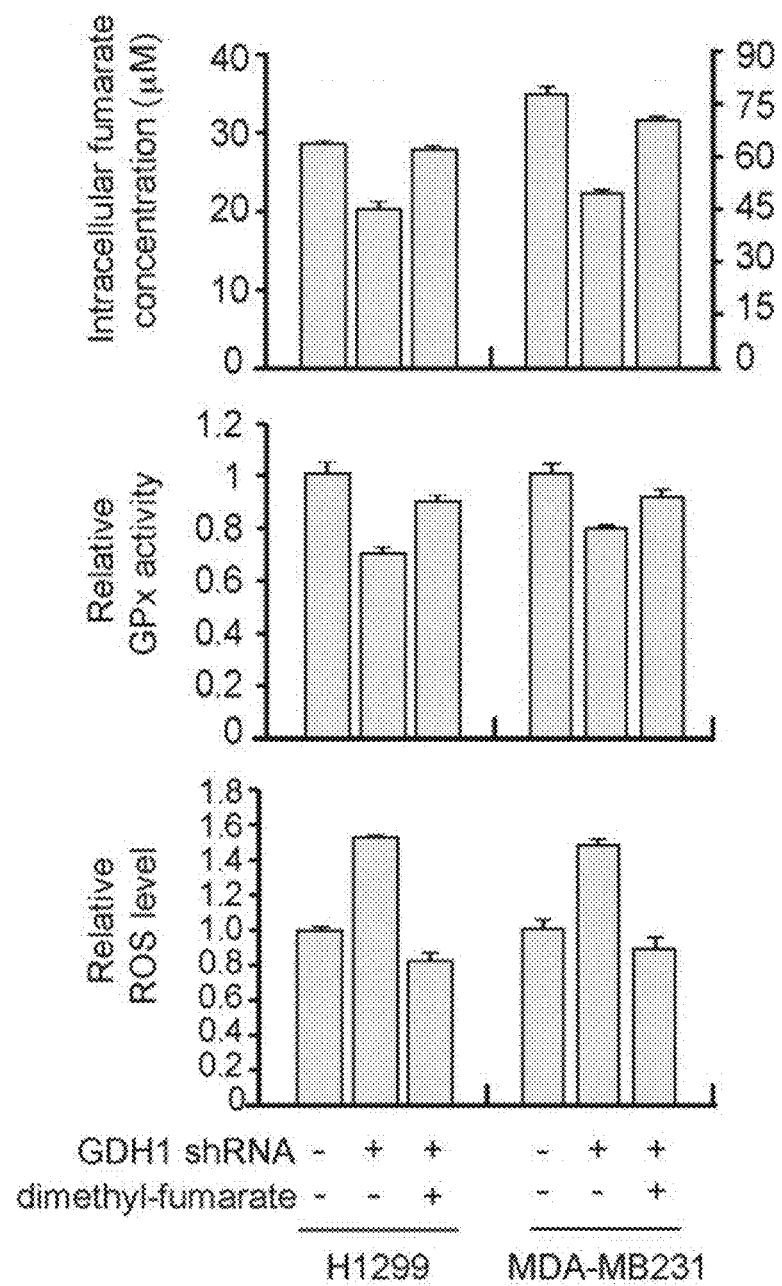
FIG. 5G shows data on intracellular fumarate levels, GPx activity, and ROS levels in cancer cells with a stable knockdown of GDH1 determined in the presence or absence of cell-permeable dimethyl-fumarate.

To examine whether fumarate binds to and activates GPx1, a radiometric metabolite-protein interaction analysis was performed using $^{14}$C-labeled metabolites incubated with GPx1 enriched from cells. Labeled fumarate but not alpha-KG, succinate, or malate was retained on GPx1, suggesting that fumarate directly binds to GPx1 (FIG. 5D). The Kd value of the GPx1-fumarate interaction was calculated to be 75.52±5.22 microM. To determine the selectivity of fumarate binding to GPx 1, a GPx1 mutant was generated with substitutions at T143 and D144. These residues are predicted to be critical for fumarate binding to GPx1 by a molecular docking study. Mutational studies demonstrated that GPx1 T143A/D144A (2A) was resistant to fumarate binding and the enzyme activity was no longer enhanced by fumarate (FIGS. 5E). This indicates that the GPx1-fumarate interaction is required for fumarate induced GPx1 activation. Furthermore, knockdown of succinate dehydrogenase A (SDHA), which produces fumarate in the TCA cycle abolished the rescue effect of methyl-alpha-KG in GDH1 knockdown cells (FIG. 5F). Consistently, decreased fumarate levels in GDH1 knockdown cells were rescued by cell-permeable dimethyl-fumarate (FIG. 5G), leading to partially rescued GPx activity and decreased ROS level in these cells (FIG. 5G). These data together indicate that GDH1 plays an important role in redox regulation by activating GPx1 through controlling intracellular levels of alpha-KG and fumarate.

Identification and Characterization of R162 as a Small Molecule Inhibitor of GDH1

Figure 6A:
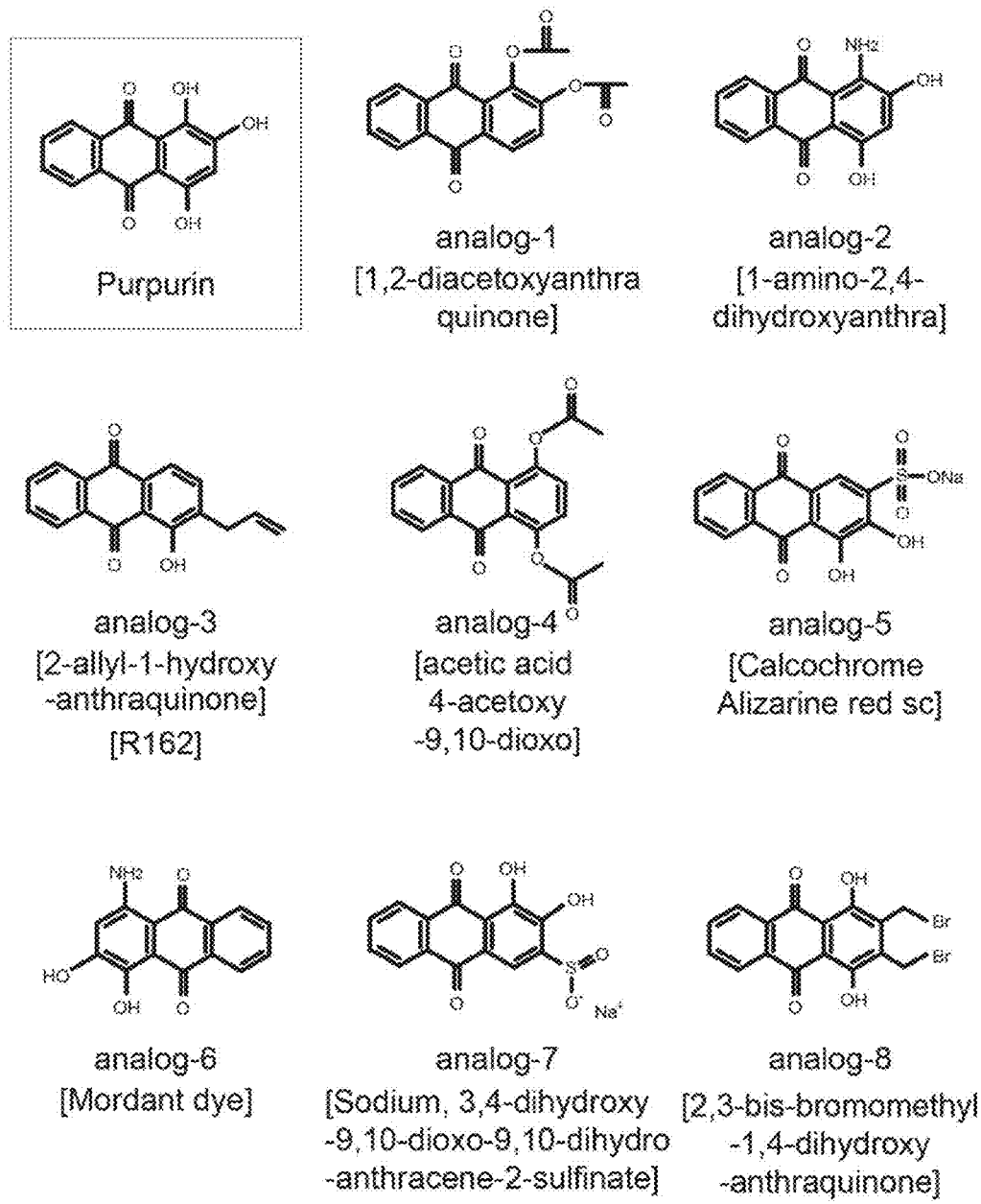
FIG. 6A illustrates embodiments of the disclosure.
Figure 6B:
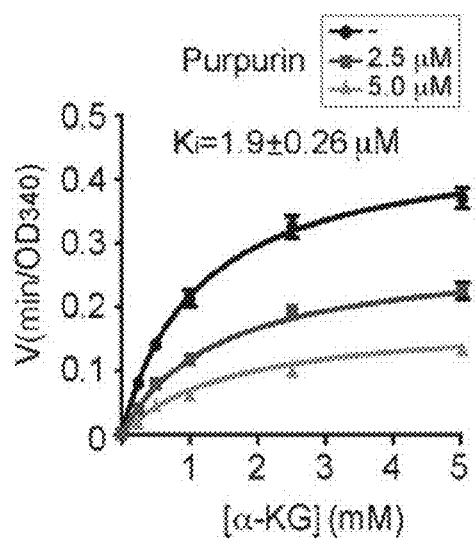
FIG. 6B shows data indicating R162 is a molecule Inhibitor of GDH1. Activity of purified GDH1 in the presence of different concentrations of alpha-KG and purpurin.
Figure 6C:
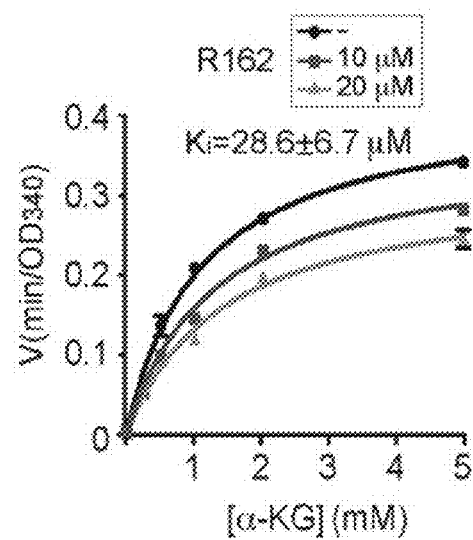
FIG. 6C shows data on R162.
Figure 6D:
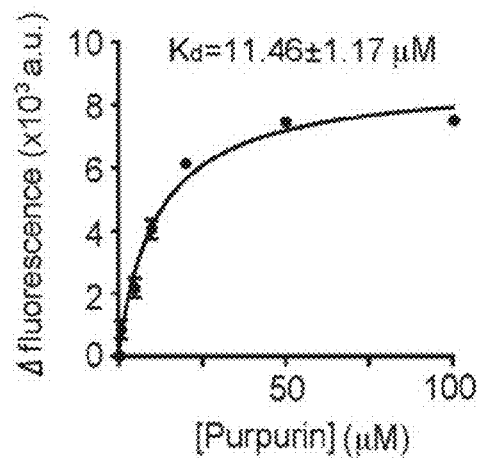
FIG. 6D shows data on Kd values determined by tryptophan fluorescence binding assay. Purified GDH1 was incubated with increasing concentrations of purpurin.
Figure 6E:
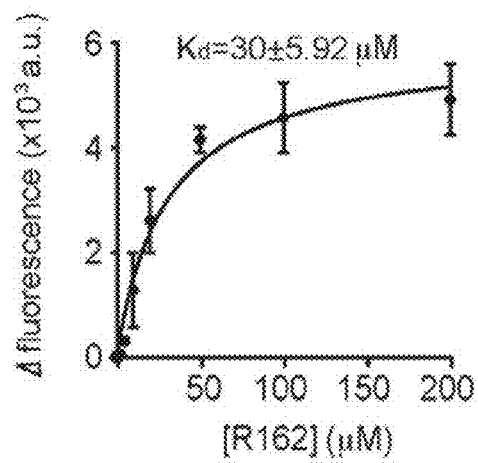
FIG. 6E shows data for R162.
Figure 6F:
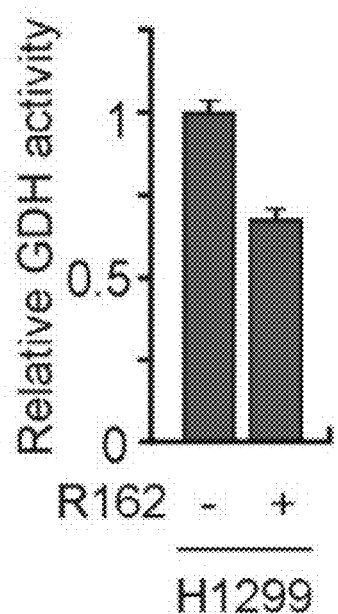
FIG. 6F shows GDH activity in cancer cells treated with R162 (20 microM).
Figure 6G:
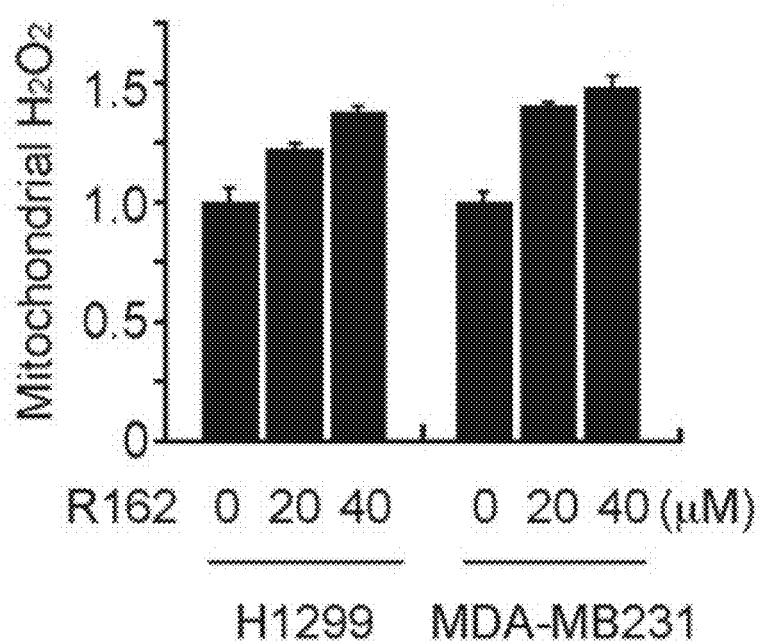
FIG. 6G shows data on mitochondrial ROS levels in H1299 and MDA-MB231 cells in the presence of R162.

Because GDH1 is upregulated in human cancers and that attenuation of GDH1 impacts cancer cell proliferation and tumor growth, GDH1 inhibition is a promising anticancer target. The only reported GDH1 inhibitor is epigallocatechin gallate (EGCG), a polyphenol flavonoid isolated from green tea. However, EGCG targets a group of enzymes that use NADPH as a cofactor. A series of screening assays were designed to identify GDH1-selective inhibitors. A small molecule compound, purpurin, was identified as a GDH1 inhibitor from a library of 2,000 Food and Drug Administration-approved small molecule compounds. Purpurin derivatives were designed (FIGS. 6A). Purpurin demonstrated dramatic inhibitory effects on the enzyme activity of recombinant, purified active GDH1 proteins in an in vitro GDH activity assay with Ki and Kd 1.9 ±0.26 and 11.46±1.17 micorM, respectively (FIGS. 6B and 6D). Although purpurin showed dramatic inhibitory effect on GDH1 enzyme activity in vitro, the compound was not cell permeable. Therefore, the purpurin analog R162, was identified as a potent GDH1 inhibitor from a group of purpurin derivatives (FIGS. 6A, 6C, and 6E). R162, which is more cell-permeable than purpurin due to its allyl group, demonstrated more potent inhibitory effects on mitochondrial GDH activity and elevated ROS levels in cancer cells (FIGS. 6F and 6G). Purpurin specifically inhibits activity of GDH but not other NADPH-dependent enzymes such as 6-phosphogluconate dehydrogenase (6PGD) and fumarate hydratase (FH) in vitro, whereas EGCG significantly affected activity of 6PGD and FH in vitro. Moreover, comparison of purpurin, R162, and EGCG demonstrated that purpurin and its analog, R162, are more potent and specific for GDH1 inhibition in vitro and in cancer cells.

Figure 6H:
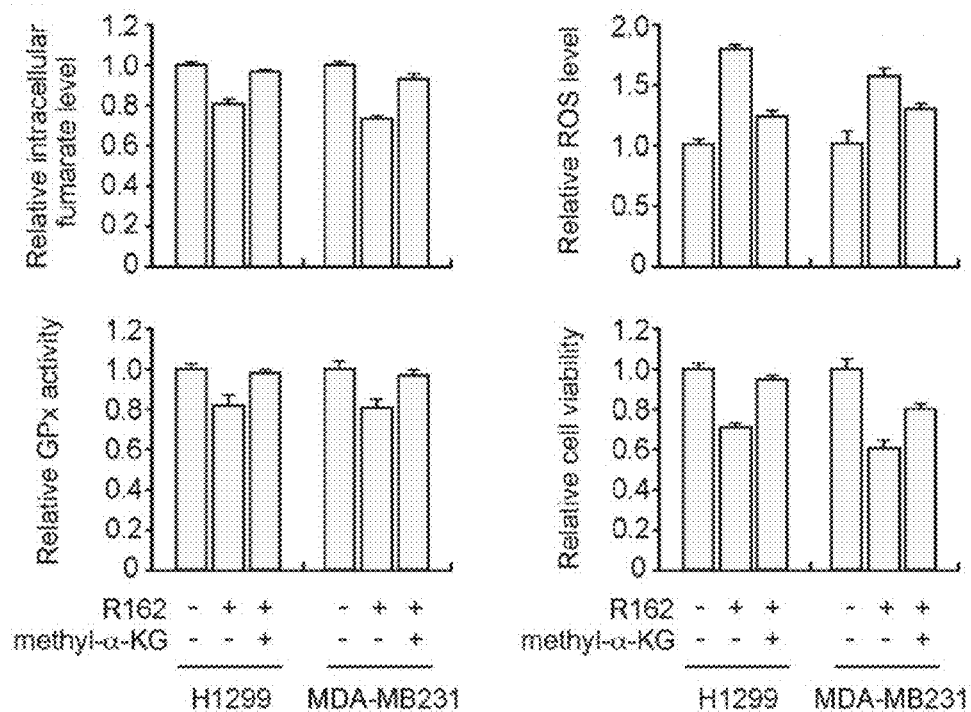
FIG. 6H shows data on methyl-alpha-KG treatment (1 mM) and intracellular fumarate levels, GPx activity, ROS levels, and cell proliferation in R162-treated H1299 and MDA-MB231 cells.
Figure 6I:
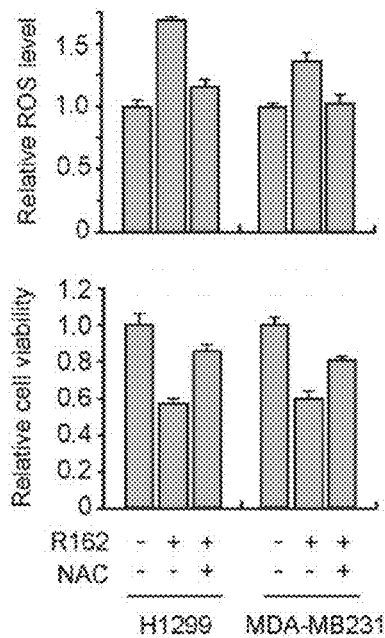
FIG. 6I shows data on NAC treatment (3 mM) on ROS level and cell proliferation in R162-treated cells.

To examine the interaction between GDH1 and R162, a thermal melt shift assay was performed. Incubating GDH1 with increasing concentrations of R162 raised the melting temperature (Tm) in a dose-dependent manner, suggesting that R162 directly binds to GDH1. In addition, in a competitive binding assay where R162 was incubated with purified GDH1 protein in the presence of different concentrations of GDH1 substrate alpha-KG, the Lineweaver-Burk plot shows that R162 acts as a mixed model inhibitor of GDH1. Inhibition of GDH1 activity by R162 treatment results in decreased intracellular fumarate levels, attenuated GPx activity, increased ROS levels, and reduced cell proliferation in H1299 and MDA-MB231 cells, which could be significantly rescued by methyl-alpha-KG treatment (FIG. 6H) as well as by antioxidant NAC (FIG. 6I). These data are essentially consistent with the phenotypes observed in GDH1 knockdown cells, suggesting that R162 targets GDH1 to disrupt redox balance through GPx1 and inhibit cancer cell proliferation.

Cell Viability in Human Peripheral Blood Samples

R162 attenuated cell viability in a group of human lung cancer, breast cancer, and leukemia cell lines, but not in human proliferating cells, including human keratinocyte (HaCaT), human fetal lung fibroblast (MRC-5), and human foreskin fibroblast cells (HFF), which serve as control proliferative human cells. Furthermore, inhibiting GDH1 by R162 also resulted in decreased cell viability of primary leukemia cells from myeloid leukemia patients, but did not affect cell viability of mononucleocytes in peripheral blood samples from healthy human donors. These data suggest the antiproliferative potential of R162 in human cancer cells with minimal toxicity.

TABLE 1

Results of hematology blood test of R162 or vehicle control-treated mice.

| | normal range | vehicle control | R162 (30 mg/kg/day) |
|---|---|---|---|
| WBC (×10$^3$/μl) | 1.8-10.7 | 4.91 ± 2.64 | 5.33 ± 0.41 |
| NEU (×10$^3$/μl) | 0.1-2.4 | 1.15 ± 0.84 | 1.71 ± 0.18 |
| LYM (×10$^3$/μl) | 0.9-9.3 | 3.46 ± 1.81 | 3.145 ± 0.10 |
| MONO (×10$^3$/μl) | 0.0-0.4 | 0.165 ± 0.03 | 0.165 ± 0.007 |
| RBC (×10$^6$/μl) | 6.36-9.42 | 7.705 ± 3.04 | 8.3 ± 0.60 |
| Eosinophils (×10$^3$/μl) | 0.0-0.2 | 0.1 ± 0.02 | 0.21 ± 0.07 |
| Basophils (×10$^3$/μl) | 0.0-0.2 | 0.025 ± 0.02 | 0.105 ± 0.06 |
| HGB (g/dl) | 11.0-15.1 | 10.3 ± 5.09 | 11.1 ± 1.55 |
| HCT (%) | 35.1-45.4 | 42.65 ± 17.88 | 45.95 ± 3.74 |
| MCV (fl) | 45.4-60.3 | 55.05 ± 1.48 | 55.35 ± 0.49 |
| MCH (pg) | 14.1-19.3 | 13.1 ± 1.41 | 13.35 ± 0.91 |
| MCHC (g/dl) | 30.2-34.2 | 23.7 ± 1.97 | 24.1 ± 1.41 |
| RDW (%) | 12.4-27.0 | 16.45 ± 0.35 | 18.5 ± 0.56 |
| MPV (fl) | 5.0-20.0 | 5.7 ± 0.56 | 6.05 ± 0.21 |

Treatment of Xenograft Tumor Mouse Models

The in vivo efficacy of R162 in the treatment of xenograft tumor mouse models was tested. For initial in vivo toxicity studies, 30 mg/kg/day of R162 was administered to mice for 30 days by intraperitoneal injection. The chronic R162 treatment did not result in a significant histopathological change between the vehicle-treated and R162-treated groups, nor altered complete blood counts, or hematopoietic properties, indicating minimal toxicity of R162 in vivo.

An in vivo R162 treatment was performed using H1299-xenograft nude mice. A day after xenograft injection, mice were divided into two groups (n=8 per group) and treated with either R162 (20 mg/kg/day) or control DMSO for 35 days. R162 treatment resulted in significantly decreased tumor growth and masses in mice compared with control mice (FIG. 7A,-7B). Moreover, R162 effectively inhibited GDH1 activity in resected tumors from xenograft nude mice (FIG. 7C). These results together suggest that R162 is a GDH1 inhibitor with promising antiproliferative potential in cancer cells with minimal toxicity in vitro and in vivo.

The invention claimed is:

1. A method of treating cancer comprising administering an effective amount of 2-allyl-1-hydroxyanthracene-9,10-dione or salts thereof to a subject in need thereof.

2. The method of claim 1 wherein the inhibitor is administered in combination with a second chemotherapeutic agent.

3. The method of claim 2, wherein the second chemotherapeutic agent is gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

4. The method of claim 1, wherein the cancer is selected from the group consisting of leukemia, cervical, ovarian, colon, breast, gastric, lung, skin, ovarian, pancreatic, prostate, and renal cancer.

* * * * *